United States Patent
Skulachev et al.

(10) Patent No.: US 9,233,903 B2
(45) Date of Patent: *Jan. 12, 2016

(54) PHARMACEUTICAL SUBSTANCES ON THE BASIS OF MITOCHONDRIA-ADDRESSED ANTIOXIDANTS

(75) Inventors: Maxim V. Skulachev, Moscow (RU);
Vladimir P. Skulachev, Moscow (RU);
Andrei A. Zamyatin, Moscow (RU);
Evgeny S. Efremov, Moscow (RU);
Vadim N. Tashlitsky, Moscow (RU);
Lev S. Yaguzhinsky, Moscow (RU);
Galina A. Korshunova, Moscow (RU);
Natalya V. Sumbatyan, Moscow (RU);
Yury N. Antonenko, Moscow (RU);
Inna I. Severina, Moscow (RU); Boris V. Chernyak, Moscow (RU)

(73) Assignee: Mitotech SA, Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 13/470,823

(22) Filed: May 14, 2012

(65) Prior Publication Data
US 2012/0259110 A1 Oct. 11, 2012

Related U.S. Application Data

(63) Continuation-in-part of application No. PCT/RU2009/000621, filed on Nov. 13, 2009.

(51) Int. Cl.
| C07C 50/04 | (2006.01) |
| C07C 46/06 | (2006.01) |
| C07D 487/22 | (2006.01) |
| A61K 47/48 | (2006.01) |
| G01N 33/50 | (2006.01) |

(52) U.S. Cl.
CPC ........... *C07C 50/04* (2013.01); *A61K 47/48023* (2013.01); *C07C 46/06* (2013.01); *C07D 487/22* (2013.01); *G01N 33/5079* (2013.01)

(58) Field of Classification Search
CPC ...................................................... C07F 9/062
See application file for complete search history.

(56) References Cited

U.S. PATENT DOCUMENTS

| 5,538,974 A | 7/1996 | Ogawa et al. |
| 6,331,532 B1 | 12/2001 | Murphy et al. |
| 7,109,189 B2 | 9/2006 | Murphy et al. |
| 2002/0044913 A1 | 4/2002 | Hamilton |
| 2005/0065099 A1 | 3/2005 | Walkinshaw et al. |
| 2007/0259908 A1 | 11/2007 | Fujii et al. |
| 2007/0270381 A1 | 11/2007 | Murphy et al. |
| 2008/0176929 A1 | 7/2008 | Skulachev et al. |
| 2008/0275005 A1 | 11/2008 | Murphy et al. |

FOREIGN PATENT DOCUMENTS

| EP | 1047701 B1 | 5/2005 |
| EP | 1534720 A1 | 6/2005 |
| EP | 1321138 B1 | 4/2006 |
| RU | 2318500 C2 | 3/2008 |
| WO | 99/26582 A2 | 6/1999 |
| WO | 2004/014927 A1 | 2/2004 |
| WO | 2006/005759 A2 | 1/2006 |
| WO | 2007/046729 A1 | 4/2007 |
| WO | 2008/048134 A1 | 4/2008 |
| WO | 2009/005386 A1 | 1/2009 |
| WO | 2009/158348 A1 | 12/2009 |

OTHER PUBLICATIONS

International Search Report, PCT/RU2008/000706, Aug. 13, 2009 (3 pages).
PCT International Search Report and Written Opinion of the International Searching Authority for PCT Application No. PCT/RU2006/000546, mailed Jul. 5, 2007, 14 pages.
International Search Report and Written Opinion of the International Searching Authority, PCT/RU2009/000295, Feb. 25, 2010, 7 pages.
International Search Report and Written Opinion, PCT/RU2009/000621, dated Aug. 12, 2010 (12 pages).
Havens et al. (2006) "Regulation of Late G1/S Phase Transition and APCCdh1 by Reactive Oxygen Species," Mol. Cell. Biol., 26(12):4701-4711.
PubChem compound CID 388445; Mar. 26, 2005 [retrieved from http://pubchem.ncbi.nlm.nih.gov/summary/summary.cgi?cid=38845&loc=ec_rcs on Jul. 31, 2012] whole doc (4 pages).
International Search Report and Written Opinion of the International Searching Authority, PCT/US12/40711, Aug. 20, 2012 (9 pages).
Adlam et al. (2005) "Targeting an antioxidant to mitochondria decreases cardiac ischennia-reperfusion injury," FASEB J., 19:1088-1095.
Agapova et al. (2008) "Mitochondria-Targeted Plastoquinone Derivatives as Tools to Interrupt Execution of the Aging Program. 3. Inhibitory Effect of SkQ1 on Tumor Development From p53-Deficient Cells," Biochem. (Mosc)., 73 (12):1300-1316 (+ 3 fig. pages).

(Continued)

Primary Examiner — Brian McDowell
(74) Attorney, Agent, or Firm — Ann-Louise Kerner; DLA Piper LLP (US)

(57) ABSTRACT

The present disclosure provides purified pharmaceutical preparations comprising oxidized SkQ1, wherein no individual impurity exceeds 1.5%, the total impurity content of the preparation does not exceed 4.0%, and the content of reduced SkQ1 is not greater than 10%, the structure of oxidized SkQ1 being:

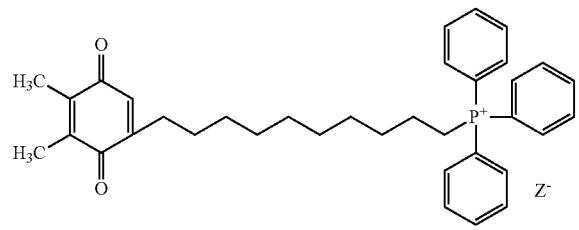

6 Claims, 20 Drawing Sheets

(56) References Cited

OTHER PUBLICATIONS

Anisimov (2007) "Molecular and Physiological Mechanisms of Aging," Antioksidanty, Nov. 27, 2007, [on line] http://imquest.alfaspace.net/BOOK/MFMA/mfma_3_9_2.htm?embedded=yes translated from Russian to English.
Antonenko et al. (2008) "Protective effects of mitochondria-targeted antioxidant SkQ in aqueous and lipid membrane environments," J. Membr. Biol., 222:141-149.
Kasahara, et al. (2005) "Manganese Superoxide Dismutase protects against oxidation-induced apoptosis in mouse retinal pigment epithelium: implications for age-related macular degeneration," Author Manuscript, NIH Public Access PMC Nov. 1, 2005 : 1-18, Invest. Ophthalmol. Vis. Sci., 46(9):3426-3434.
Holloszy (1998) "Longevity of exercising male rats: effect of an antioxidant supplemented diet," Mechanisms of Ageing and Development, 100:211-219.
King et al. (2004) "Mitochondria-derived reactive oxygen species mediate blue light-induced death of retinal pigment epithelial cells," Photochem. and Photobiol., 79(5):470-475.
Li et al. (2000) "Skeletal muscle respiratory uncoupling prevents diet-induced obesity and insulin resistance in mice," Nat. Med. 6(10):1115-1120.
Liu et al. (1993) "Age-associated changes in superoxide dismutase activity, thiobarbituric acid reactivity and reduced glutathione level in the brain and liver in senescence accelerated mice (SAM): a comparison with ddY mice," Mech. Ageing & Dev., 71:23-30.
Longo et al. (2005) "Programmed and altruistic ageing," Nature Reviews Genetics, 6:866-872.
Kirschner et al. (1994) "Role of iron and oxygen-derived free radicals in ischemia-reperfusion injury" J. Am. Coll. Surg., 179:103-117.
Popova et al. (2010) "Scavenging of Reactive Oxygen Species in Mitochondria Induces Myofibroblast Differentiation," Antiox. & Redox. Signal., 13(9):1297-1307.
Popova et al. (2006) "MitoQ induced miofibroblast differentiation of human fibroblasts," Biochimica et Biophysica Acta, S:433-434.
Reliene et al. (2007) "Antioxidants suppress lymphoma and increase longevity in atm-deficient mice," J. Nutrition, 137:229S-232S.
Reddy (2006) "Mitochondrial oxidative damage in aging and Alzheimer's disease: implications for mitochondrially targeted antioxidant therapeutics," J. Biomedicine and Biotech., Art.ID 31372:1-13.
Skulachev (2003) "Aging and the programmed death phenomena," Topics in Current Genetics, vol. 3, Nystrom and Osiewacz, Eds., Model systems in Aging, Springer-Verlag Berlin Heidelberg 191-238.
Starkov et al. (1997) "6-ketocholestanol is a recoupler for mitochondria, chromatophores and cytochrome oxidase proteoliposomes," Biochim. Biophys. Acta. 1318:159-172.
Tompkins et al. (2006) "Mitochondrial dysfunction in cardiac ischemia-reperfusion injury: ROS from complex I, without inhibition," Dothan Biophys. Acta. 1762:223-231.
Sidorova et al. (2004) "Transcriptional activation of cytochrome P450 1A1 with alpha-tocopherol," Bull Exp. Bio. Med., 138(3):233-236.
Mecocci et al. (2000) "Plasma antioxidants and longevity: a study on healthy centenarians," Free Radical Biology and Medicine, 28(8):1243-1248.
Pozniakovsky et al. (2005) "Role of mitochondria in the pheromone- and amiodarone-induced programmed death of yeast," J. Cell Biol., 168(2):257-69.
Orr et al. (2003) "Effects of overexpression of copper-zinc and manganese superoxide dismutases, catalase, and thioredoxin reductase genes on longevity in Drosophila melanogaster," J. Biol. Chem., 278(29):26418-26422.
Papp et al. (1999) "Glutathione status in retinopathy of prematurity," Free Radic. Biol. & Med., 27(7-8):738-743.
Petrosillo et al. (2005) "Mitochondrial dysfunction associated with cardiac ischemia/reperfusion can be attenuated by oxygen tension control. Role of oxygen-free radicals and cardiolipin," Biochimica et Biophysica Acta, 1710:78-86.

Petrosillo et al. (2006) "Protective effect of melatonin against mitochondrial dysfunction associated with cardiac ischemia-reperfusion: role of cardiolipin," FASEB J., 20:269-276.
Sheu et al. (2006) "Targeting antioxidants to mitochondria: a new therapeutic direction," Biochimica et Biophysica Acta, 1762:256-265.
Yildirim et al. (2005) "Role of oxidative stress enzymes in open-angle glaucoma," Eye, 19:580-583.
Zweier et al. (1987) "Direct measurement of free radical generation following reperfusion of ischemic myocardium," PNAS USA, 84:1404-1407.
Riess et al. (2004) "Reduced reactive O2 species formation and preserved mitochondrial NADH and [Ca2+] levels during short-term 17° C ischemia in intact hearts," Cardiovascular Research, 61:580-590.
Sundaresan et al. (1995) "Requirement for Generation of H2O2 for Platelet-Derived Growth Factor Signal Transduction," Science, 270:296-299.
International Search Report and Written Opinion of the International Searching Authority, PCTIRU2007/000044, Nov. 1, 2007 (9 Pages).
International Search Report dated Dec. 20, 2007 and International Preliminary Report on Patentability dated Nov. 10, 2009, PCT/RU2007/000171 (16 pages).
International Search Report and Written Opinion of the International Searching Authority, PCT/RU2007/000355, Mar. 27, 2008 (10 pages).
PCT International Search Report mailed Nov. 1, 2007 and International Preliminary Report on Patentability issued Aug. 4, 2009 for PCT Application No. PCT/RU2007/000043, 9 pages.
Skulachev (2005) "Critical Review: How to Clean the Dirtiest Place in the Cell: Cationic Antioxidants as Intramitochondrial ROS Scavengers," IUBMB Life, 57(4/5):305-310.
Skulachev (2007) "A Biochemical Approach to the Problem of Aging: 'Megaproject' on Membrane-Penetrating Ions. The First Results and Prospects," Biochem. (Moscow), 72(12):1385-1396.
Lou et al. (2007) "Mitochondrial Uncouplers With an Extraordinary Dynamic Range," Biochem. J., 407:129-140.
Neroev et al. (2008) Mitochondria-Targeted Plastoquinone Derivatives as Tools to Interrupt Execution of the Aging Program. 4. Age-Related Eye Disease. SkQ1 Returns Vision to Blind Animals, Biochemistry (Mosc.), 73 (12):1317-1328.
International Search Report and Written Opinion, PCT/RU2006/000394, dated Nov. 2, 2006 (6 pages).
International Search Report and Written Opinion, PCT/RU2006/000547, dated Jul. 5, 2007 (7 pages).
Berge et al. (1977) "Pharmaceutical Salts," J. Pharma. Sci., 66(1):1-19.
Blaikie et al. (2006) "Targeting Dinitrophenol to Mitochondria: Limitations to the Development of a Self-limiting Mitochondrial Protonophore," Biosci. Rep., 26:231-243.
Brand et al. (1992) "The mechanism of the increase in mitochondrial proton permeability induced by thyroid hormones," Eur. J. Biochem. 206:775-781.
Hansford et al. (1997) "Dependence of H2O2 formation by rat heart mitochondria on substrate availability and donor age," J. Bioenerg. Biomem. 29(1):89-95.
Antonenko et al. (2008) "Mitochondria-Targeted Plastoquinone Derivatives as Tools to Interrupt Execution of the Aging Program. 1. Cationic Plastoquinone Derivatives: Sythesis and in vitro Studies," Biochemistry, 73(12)1273-1287.
Doughan et al. (2007) "Original Research Communication: Mitochondrial Redox Cycling of Mitoquinone Leads to superoxide Production and Cellular Apoptosis," Antioxid. & Redox Signal., 9(11):1825-1836.
Green et al. (2004) "Prevention of Mitochondrial Oxidative Damage as a Therapeutic Strategy in Diabetes," Diabetes, 53(1):S110-S118.
Bakeeva et al. (2008) "Mitochondria-targeted plastoquinone derivatives as tools to interrupt execution of the aging program. 2. Treatment of some ROS- and Age-related diseases (heart arrhythmia, heart infarctions, kidney ischemia, and stroke)," Biochemistry (Moscow), 73(12):1288-1299 and 1 figure.

(56) References Cited

OTHER PUBLICATIONS

Clem et al. (2008) "Small-molecule inhibition of 6-phosphofructo-2-kinase activity suppresses glycolytic flux and tumor growth," Mol. Canc. Ther. 7(1):110-120.

Goldstein (2002) "Reactive oxygen species as essential components of ambient air," Biochemistry (Mosc.) 67:161-170.

Green (1974) "The electromechanochemical model for energy coupling in mitochondria," Biochimica et Biophysica Acta, 346:27-78.

Kirste et al. (1995) "Continuous-wave electron spin resonance studies of porphyrin and porphyrin-quinone triplet states," J. Chem. Soc. Perkin Trans. 2:2147-2152.

Murphy et al. (2007) Targeting antioxidants to mitochondria by conjugation to lipophilic cations. Annu. Rev. Pharmacol. Toxicol., 47:629-656.

Plotnikov et al. (2008) "Interrelations of Mitochondrial Fragmentation and Cell Death Under Ischemia/Reoxygenation and UV-Irradiation: Protective Effects of SkQ1, Lithium Ions and Insulin," FEBS Letters, 582:3117-3124.

Plotnikov et al. (2010) "New-generation Skulachev ions exhibiting nephroprotective and neuroprotective properties." Biochemistry (Mosc.), 75(2):145-150.

Skulachev et al. (2005) "Aging as mitochondria-mediated atavistic program. Can aging be switched off?" Ann. N.Y. Acad. Sci., 1057:145-164.

Skulachev et al. (2009) "An attempt to prevent senescence: a mitochondrial approach," Biochimica et Biophysica Acta., 1787:437-461.

Smith et al. (2008) "Mitochondria-targeted antioxidants in the treatment of disease,"Ann. N.Y. Acad. Sci., 1147:105-111.

Snow et al. (2010) "A double-blind, placebo-controlled study to assess the mitochondria-targeted antioxidant MitoQ as a disease-modifying therapy in Parkinson's disease," Mov. Disord. 25(11):1670-1674.

Stefanova et al. (2010) "Behavioral effects induced by mitochondria-targeted antioxidant SkQ1 in Wistar and senescence-accelerated OXYS rats," J. Alzheimer's Dis. 21:479-491.

Tauskela (2007) "MitoQ—a mitochondria-targeted antioxidant," IDrugs, 10:399-412.

Triet et al. (1993) "Anxiogenic stimuli in the elevated plus-maze," Pharmacol. Biochem. & Behav. 44:463-469.

Senge et al. (1999) "Structure and Conformation of Photosynthetic Pigments and Related Compounds. 12. A Crystallographic Analysis of Porphyrin-quinones and Their Precursors," Photochem. & Photobiol., 70(2):206-216.

Kurreck et al. (1995) "Mimicking primary processes in photosynthesis covalently linked porphyrin quinones," Radiation Physics and Chemistry, 45(6):853-865.

Kurreck et al. (1995) "Mimicking primary processes in photosynthesis. Photochemistry of covalently linked porphyrin quinones studied by EPR spectroscopy," Solar Energy Materials and Solar Cells, 38:91-110.

O'Hanley et al. (1996), "Prospects for urinary tract infection vaccines. In: Urinary Tract Infections: Molecular Pathogenesis and Clinical Management," (Mobley, H. L. T. & Warren, J.W., eds), (Washington, DC: ASM Press), pp. 405-425 (23 pages).

O'Hanley et al. (1991), "Alpha-hemolysin contributes to the pathogenicity of piliated digalactoside-binding Escherichia coli in the kidney: efficacy of an alpha-hemolysin vaccine in preventing renal injury in the BALB/c mouse model of pyelonephritis," Infect. Immun. 59:1153-1161.

Okada et al. (2005) "The implications of the upregulation of ICAM-1/VCAM-1 expression of corneal fibroblasts on the pathogenesis of allergic keratopathy," Invest. Ophthalmol. Vis. Sci., 46(12):4512-4518.

Smith, et al. (2003) "Delivery of bioactive molecules to mitochondria in vivo," PNAS, 100(9):5407-5412.

Zorov et al. (2006), "Mitochondrial ROS-induced ROS release: an update and review," Biochim. Biophys. Acta. 1757:509-517.

Zorov et al. (2000), "Reactive oxygen species (ROS)-induced ROS release: a new phenomenon accompanying induction of the mitochondrial permeability transition in cardiac myocytes," J. Exp. Med. 192:1001-1014.

Viana et al. (2004) "Hypoglycemic and anti-lipemic effects of the aqueous extract from Cissus sicyoides," BMC Pharmacol. 4:9 (7 pages).

Spector (1995) "Oxidative stress-induced cataract: mechanism of action," FASEB J., 9:1173-1182.

Vollset et al. (2000) "Plasma total homocysteine, pregnancy complications, and adverse pregnancy outcomes: the Hordaland Homocysteine study," Am. J. Clin. Nutr., 71:962-968.

Vanden Hoek et al. (1996) "Reperfusion injury in cardiac myocytes after simulated ischemia," Am. J. Phys., 270:1334-1341.

Villa et al. (2004) "Animal models of endotoxic shock" Meth. Mol. Med., 98:199-206.

Spencer et al. (1998) "Transition metal chelators reduce directly measured myocardial free radical production during reperfusion," J. Cardiovasc. Pharmacol., 32(3):343-348.

Stella et al. (2007) Prodrugs: Challenges and Rewards, Springer, New York Part 1 and 2 (17 pages).

Usdh (2005) Guidance for Industry: Estimating the Maximum Safe Starting Dose in Initial Clinical Trials for Therapeutics in Adult Healthy Volunteers, U.S. Dept. of Health and Human Services, FDA, CDER (30 pages).

Weyer et al. (1999) "Development of beta3-adrenoceptor agonists for the treatment of obesity and diabetes—an update," Diabetes Metab., 25:11-21.

Zamzami et al. (1996), "Mitochondrial control of nuclear apoptosis," J. Exp. Med. 183:1533-1544.

Zoratti et al. (1995) "The mitochondrial permeability transition," Biochim. Biophys. Acta., 1241:139-176.

Parascandola (1974) "Dinitrophenol and bioenergetics: an historical perspective," Mol. Cell. Biochem., 5(1-2):69-77.

Petit-Demouliere et al. (2005) "Forced swimming test in mice: a review of antidepressant activity," Psychopharmacol., 177:245-255.

Poehlman et al. (1989) "A review: exercise and its influence on resting energy metabolism in man," Med. Sci. Sports Exerc., 21(4):515-525.

Rodriguez-Spong et al. (2004) "General Principles of Pharmaceutical Solid Polymorphism: A Supramolecular Perspective," Advanced Drug Delivery Reviews, 56:241-274.

Rogers (2008) "Has enhanced folate status during pregnancy altered natural selection and possibly Autism prevalence? A closer look at a possible link," Med. Hypoth., 71:406-410.

13-Methoxydihydronitidine—Compound Summary PubChem compound CID 38845; Mar. 26, 2005 [retrieved_from http://pubchem.ncbi.nlm.nih.gov/summary/summary.cgi?cid=38845&loc=ec_rcs on Jul. 31, 2012] whole doc (4 pages).

Antonenko et al. (2008) "Mitochondria-Targeted Plastoquinone Derivatives as Tools to Interrupt Execution of the Aging Program. 1. Cationic Plastoquinone Derivatives: Sythesis and in vitro Studies," Biochemistry (Moscow), 73(12) 1273-1287.

Astrup et al. (1996) "Low resting metabolic rate in subjects predisposed to obesity: a role for thyroid status 1-3," Am. J. Clin. Nutr. 63:879-883.

Maire et al. (2001) "Factors associated with hyperhomocysteinemia in Crohn's disease," Gastroenterol. Clin. Biol., 25 (8-9):745-748 (French-abstract only, 1 page).

Bacsi et al. (2005) "Effect of pollen-mediated oxidative stress on immediate hypersensitivity reactions and late-phase inflammation in allergic conjunctivitis," J. Allergy Clin. Immunol., 116(4): 836-843.

Barclay et al. (2003) Phenols as antioxidants. In the Chemistry of Phenols, Part 2, Rappoport, Z Ed., Wiley, pp. 875 (3 pages).

Becker (2004) "New concepts in reactive oxygen species and cardiovascular reperfusion physiology" Cardiovascular Research, 61:461-470.

Dugina et al. (2009) "β- and γ-Cyoplasmic Actins Display Distinct Distribution and Functional Diversity," J. Cell Sci., 122(16):2980-2988.

Bernard et al. (2002) "Hytopthermia after cardiac arrest study group. Mild therapeutic hypothermia to improve the neurologic outcome after cardiac arrest," New Engl. J. Med. 346(8):549-556.

(56) References Cited

OTHER PUBLICATIONS

Bhate et al. (2008) "Vitamin B12 status of pregnant Indian women and cognitive function in their 9-year-old children," Food Nutr. Bull., 29:249-54.
Faa et al. (1999) "Iron chelating agents in clinical practice," Coordination Chemistry Reviews, 184(1):291-310.
Makhro et al. (2008) "Prenatal Hyperhomocysteinemia as a Model of Oxidative Stress of the Brain," Bull. Exper. Biol. & Med., 146(1):33-35.
Malenka et al. (1999) "Long-term potentiation: a decade of progress?" Science, 285(5435):1870-1874.
Bray et al. (1999) "Sibutramine produces dose-related weight loss," Obes. Res. 7(2):189-198.
Byrom (1933) "Nature of myxoedema," Clin. Sci. 1:273-285.
Cherubini et al. (2005). Potential markers of oxidative stress in stroke. Free Radic Biol Med 39, 841-852.
Clapham et al. (2000) "Mice overexpressing human uncoupling protein-3 in skeletal muscle are hyperphagic and lean," Nature, 406:415-418.
Collins et al. (2004) "Heart protection study collaborative group. Effects of cholesterol-lowering with simvastatin on stroke and other major vascular events in 20536 people with cerebrovascular disease or other high-risk conditions," Lancet 363(9411):757-767.
Coulter et al. (2000) "Mitochondrially targeted antioxidants and thiol reagents," Free Rad. Biol. Med. 28 (10):1547-1554.
Demougeot et al. (2004) "Cytoprotective efficacy and mechanisms of the liposoluble iron chelator 2,2'-dipyridyl in the rat photothrombotic ischemic stroke model," J. Pharmacol. Exper. Ther. 311:1080-1087.
Denisov (2006) "Reactivity of quinones as alkyl radical acceptors," Kinetics and Catalysis, 45(5):662-671.
Matsumoto et al. (1992). Antioxidant effect on renal scarring following infection of mannose-sensitive-piliated bacteria. Nephron 60,210-215.
Dominguez (2006), "Ageing, lifestyle modifications, and cardiovascular disease in developing countries," J. Nutr. Health Aging, 10(2):143-149.
Galkina et al. (2004). Endothelium-leukocyte interactions under the influence of the superoxide-nitrogen monoxide system. Med Sci Monit 10, BR307-316.
Monaco et al. (2004) "Canonical pathway of nuclear factor kB activation selectively regulates proinflammatory and prothrombotic responses in human atherosclerosis," PNAS, 101(15):5634-5639.
Gear (1974) "Rhodamine 6G: A potent inhibitor of mitochondrial oxidative phosphorylation," J. Biol. Chem., 249 (11):3628-3637.
Giorgini et al. (2001) "Reactivity of ubiquinones and ubiquinols with free radicals." Free Rad. Res. 35:63-72.
Gong et al. (1997) "Uncoupling protein-3 is a mediator of thermogenesis regulated by thyroid hormone, beta3-adrenergic agonists, and leptin," J. Biol. Chem., 272(39):24129-24132.
Gorgone et al (2009) "Hyperhomocysteinemia in patients with epilepsy: does it play a role in the pathogenesis of brain atrophy? A preliminary report," Epilepsia, 50(1):33-36.

Griffiths et al. (2001) "Genetic analysis of collagen-induced arthritis in rats: a polygenic model for rheumatoid arthritis predicts a common framework of cross-species inflammatory/autoimmune disease loci." Immunol. Rev. 184:172-83.
Haass et al. (2007) "Soluble protein oligomers in neurodegeneration: lessons from the Alzheimer's amyloid beta-peptide." Nat. Rev. Mol. Cell. Biol. 8:101-112.
Molloy et al. (2009) "Maternal vitamin B12 status and risk of neural tube defects in a population with high neural tube defect prevalence and no folic Acid fortification," Pediatrics, 123:917-923.
Hess et al. (2002) "Biological and Chemical Applications of Fluorescence Correlation Spectroscopy: A Review," Biochem. 41(3):697-705.
Mundi et al. (1991). Extracellular release of reactive oxygen species from human neutrophils upon interaction with *Escherichia coli* strains causing renal scarring. Infect Immun 59, 4168-4172.
Hummel et al. (1966) "Diabetes, new mutation in the mouse." Science, 153:1127-1128.
Hunter et al. (1979). The Ca2+-induced membrane transition in mitochondria. I. The protective mechanisms. Arch Biochem Biophys 195, 453-459.
Hvizdos et al. (1999) "Orlistat: a review of its use in the management of obesity," Drugs, 58(4):743-760.
Johnson et al. (1980) "Localization of Mitochondria in Living Cells with Rhodamine 123," Proc. Natl. Acad. Sci. USA, 77(2):990-994.
Jolkkonen (2000) "Behavioral effects of the alpha(2)-adrenoceptor antagonist, atipamezole, after focal cerebral ischemia in rats," Eur. J. Pharmacol., 400, 211-219.
Juhaszova et al. (2004). Glycogen synthase kinase-3beta mediates convergence of protection signaling to inhibit the mitochondrial permeability transition pore. J Clin Invest 113, 1535-1549.
Murphy (1997) "Selective Targeting of Bioactive Compounds to Mitochondria," Trends in Biotechnology, 15 (8):326-330.
Karl et al. (2003) "Behavioral phenotyping of mice in pharmacological and toxicological research," Exp. Toxicol. Pathol., 55(1):69-83.
Kirkinezos et al (2001) "Reactive Oxygen species and Mitochondrial Diseases," Seminars in Cell & Developmental Biology, 12:449-457.
Kutala et al. (2006) "Prevention of postischemic myocardial reperfusion injury by the combined treatment of NCX-4016 and Tempol." J. Cardiovasc. Pharmacol., 48(3):79-87.
Oddo et al. (2003) "Triple-transgenic model of Alzheimer's disease with plaques and tangles: intracellular Abeta and synaptic dysfunction," Neuron, 39:409-421.
Kroemer et al. (1995). The biochemistry of programmed cell death. Faseb J 9, 1277-1287.
Kromhout (2001) "Diet and cardiovascular diseases," J. Nutr. Health Aging, 5:144-149.
Li et al. (2002). Activation of macrophage nuclear factor-kappa B and induction of inducible nitric oxide synthase by LPS. Respir Res 3, 23 (6 pages).
Liu et al. (1996). Induction of apoptotic program in cell-free extracts: requirement for dATP and cytochrome c. Cell 86, 147-157.
Lysenko et al. (2001) "Thrombocytopathies and their role in the development of hemorrhagic syndrome in vascular diseases of the fundus oculi," Vestn. Oftalmol., 117(1):24-26 (English Translation of Russian article abstract—1 page).

*- difference is statistically significant

PHARMACEUTICAL SUBSTANCES ON THE BASIS OF MITOCHONDRIA-ADDRESSED ANTIOXIDANTS

REFERENCE TO RELATED APPLICATIONS

This application is a continuation-in-part of International Application No. PCT/RU2009/000621, filed on Nov. 13, 2009, the entire disclosure of which is hereby incorporated by reference herein.

FIELD OF THE INVENTION

This invention relates to the fields of pharmaceutics and medicine, and, in particular, concerns the production and use of pharmaceutical substances on the basis of mitochondria-addressed compounds.

BACKGROUND

Data published to date clearly demonstrate good pharmaceutical perspectives of a new class of biologically active substances called mitochondria-addressed antioxidants (MAAs) (see Skulachev (2005) *IUBMB Life.*, 57:305-10; Skulachev (2007) *Biochemistry* (Mosc)., 72:1385-96; Antonenko et al. (2008) *Biochemistry* (Mosc)., 73:1273-87; Skulachev et al. (2009) *Biochim Biophys Acta.*, 1787:437-61; Smith et al. (2008) *Ann. N.Y. Acad. Sci.*, 1147:105-11; see also WO2007046729, WO2009005386; U.S. Pat. No. 6,331,532; EP 1047701; EP 1534720; and Green (1974) *Biochem. Biophys. Acta.*, 346:27-78).

The above-mentioned sources disclose the results of studies of MAAs under laboratory conditions in vitro or animal models. However, in order to use any compound as active pharmaceutical ingredient, the compound must meet certain requirements. For example, the compounds must comply fully with the national regulators requirements summarized in corresponding documents, pharmacopoeial monographs. The main requirements are: authenticity, impurity content, heavy metal content, water content, residual organic solvent content, sterility, method of quantitative measurement of the compound, methods of packaging, labeling and transportation.

Also, characteristics of the compound listed in regulatory documents as well as its pharmaceutical activity must remain within postulated limits during the postulated shelf storage time. Particular attention should be drawn to the total content of impurities, as well as the content of single impurities. In particular, single impurities which cannot be individually identified and fully characterized should not constitute a significant proportion (in most cases—more than 1%) of the total content of impurities.

Another significant difficulty with the practical applications of MAAs as pharmaceutical substances is that in the descriptions of inventions related to MAAs (see above), a large number of compounds claimed as mitochondria-addressed antioxidants have been disclosed, but they have different (sometimes even opposite) biological activity (for example, see Antonenko et al. (2008), *Biochem. (Mosc)*, 73:1273-87). Thus, there is a need for the development of methods for design of biologically active substances with well-defined, predetermined properties suitable for the specific application of the compound. There is also a need of methods to predict properties and biological activity (and thus, clinical activity) of MAAs on the basis of Skulachev-ions.

SUMMARY

In one aspect, the disclosure provides a purified preparation comprising at least 95% of a compound of Formula I:

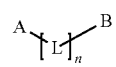

(I)

wherein:

A is an antioxidant of Formula II:

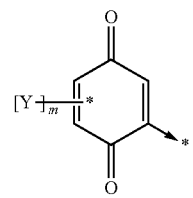

(II)

and/or reduced form thereof, wherein m comprises an integer from 1 to 3;

Y is independently selected from the group consisting of: lower alkyl, lower alkoxy, or two adjacent Y groups, together with carbon atoms to which they are attached, form a following structure of Formula III:

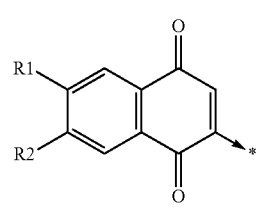

(III)

and/or reduced form thereof, wherein:

$R_1$ and $R_2$ are the same or different and are each independently lower alkyl or lower alkoxy;

L is a linker group, comprising:

a) a straight or branched hydrocarbon chain optionally substituted by one or more double or triple bond, or ether bond, or ester bond, or C—S, or S—S, or peptide bond; and which is optionally substituted by one or more substituents preferably selected from alkyl, alkoxy, halogen, keto group, amino group; or b) a natural isoprene chain;

n is an integer from 1 to 20; and

B is a targeting group comprising:

a) a Skulachev-ion Sk:

$Sk^+Z^-$, wherein:

Sk is a lipophillic cation or a lipophillic metalloporphyrin having a structure:

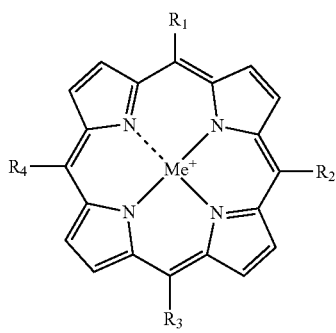

wherein Me⁺ is a metal ion selected from the group consisting of Mn, Fe, Co, Cu, Mg, and Zn; and
Z is a pharmaceutically acceptable anion; or
b) an amphiphillic zwitterion.

As used herein the term "purified preparation," encompasses an intermediate product or a final product that can be incorporated into a pharmaceutical substance, composition, or product.

In some embodiments, the compounds of Formula I are stable at room temperature for at least 14 days, at least 30 days, at least 3 months, at least 6 months, at least 1 year, or at least 2 years. In one embodiment, the compounds of Formula I are stable at room temperature for about 14 days to about 2 years. In other embodiments, the compound of Formula I is stable at about 2° C. to about 8° C. for at least 14 days, at least 30 days, at least 1 year, or at least 2 years. In certain embodiments, compound of Formula I is stable at about 2° C. to about 8° C. for about 14 days to about 2 years. In yet other embodiments, the compound of Formula I is stable at or below 0° C. for at least 14 days, at least 30 days, at least 3 months at least 6 months, at least 1 year, or at least 2 years. In certain embodiments, the compound of Formula I is stable at or below 0° C. for about 14 days to 2 years.

In some embodiments, the preparation comprises an oxidized form and a reduced form of the compound of Formula I.

In another aspect, the disclosure provides a compound of Formula II:

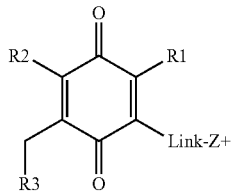
(II)

and the reduced (quinone) form thereof,
wherein:
R1 comprises a methyl group;
R2 and R3 are identical or different substituents selected from lower alkyl or lower alkoxy;
Link comprises either a straight or branched hydrocarbon chain optionally comprising one or more double or triple bond, an ether bond, an ester bond, a C—S bond, an S—S bond, or a peptide bond;
Z+ comprises a hydrophobic cation; and
the compound is not MitoQ.

In another aspect, the invention comprises a compound of Formula II:

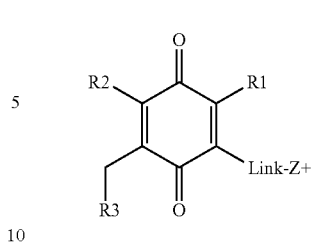
(II)

and the reduced (quinone) form thereof,
wherein:
R1 comprises a methyl group or hydrogen,
R2, or R3, or both are hydrogen;
Link comprises either a straight or branched hydrocarbon chain optionally comprising one or more double or triple bond, an ether bond, an ester bond, a C—S bond, an S—S bond, or a peptide bond;
Z+ comprises a hydrophobic cation; and
the compound is not DMQ.

A compound of Formula II:

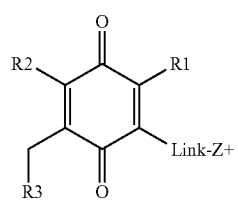
(II)

and the reduced (quinone) form thereof,
wherein:
R1 is methyl or hydrogen;
R2 and R3 are identical or different substituents selected from lower alkyl or lower alkoxy, at least one of R2 or R3 being lower alkyl;
Link comprises either a straight or branched hydrocarbon chain optionally comprising one or more double or triple bond, an ether bond, an ester bond, a C—S bond, an S—S bond, or a peptide bond;
Z+ comprises a hydrophobic cation; and
the compound is not SkQR1, SkQ3, SkQ4, SkQ5, or SkQ1.

In still another aspect, the disclosure provides a compound of Formula VIII(a):

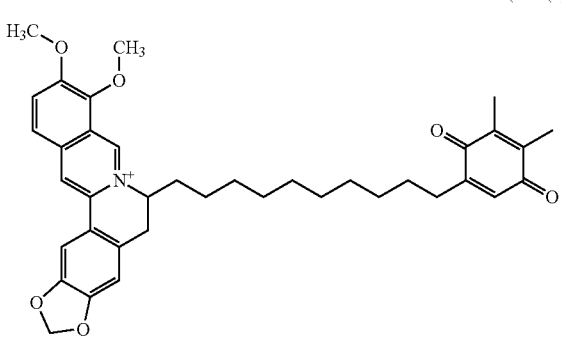
(VIII(a))

and the reduced (quinone) form thereof.

The disclosure also provides in another aspect a compound of Formula VIII(b):

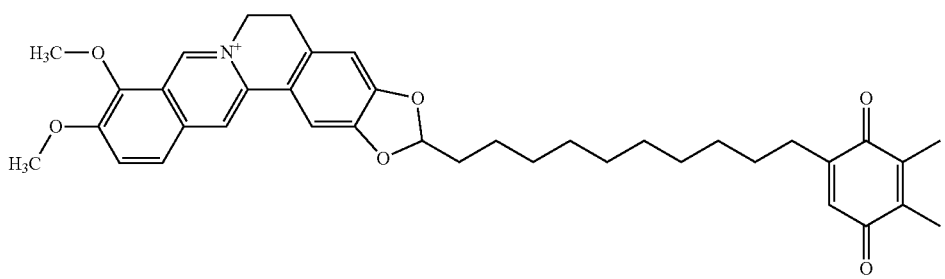

(VIII(b))

and the reduced (quinone) form thereof.

In another aspect, the disclosure provides a compound of Formula IX:

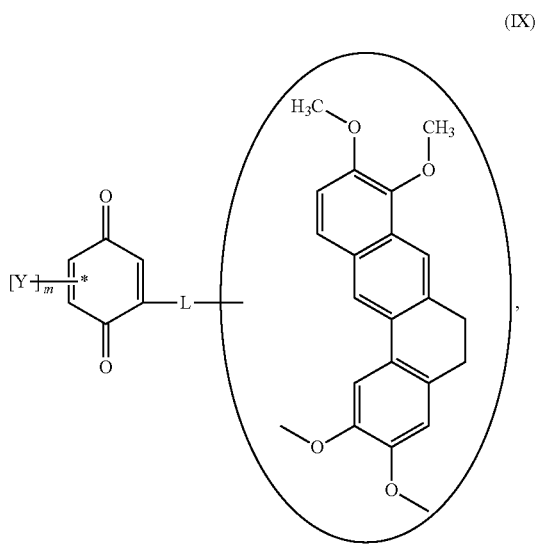

(IX)

and the reduced (quinone) form thereof,
wherein:
m is an integer from 0 to 3; and
L is a linker comprising from about 1 to about 50 units, each unit comprising:
a straight or branched hydrocarbon chain optionally containing one or more double or triple bond, ether bond, ester bond, C—S bond, S—S bond, or peptide bond; and which is optionally substituted by one or more substituents selected from the group consisting of alkyl, alkoxy, halogen, keto group, and amino group; or
a natural isoprene chain.

The disclosure also provides a compound of Formula X:

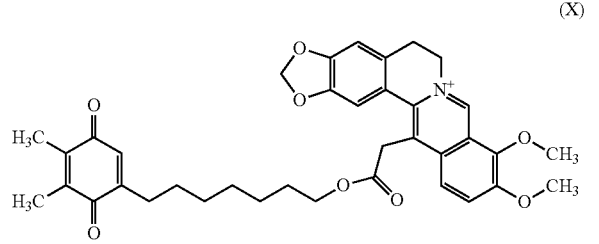

(X)

and the reduced (quinone) form thereof.

In addition, the disclosure provides a compound of Formula XI:

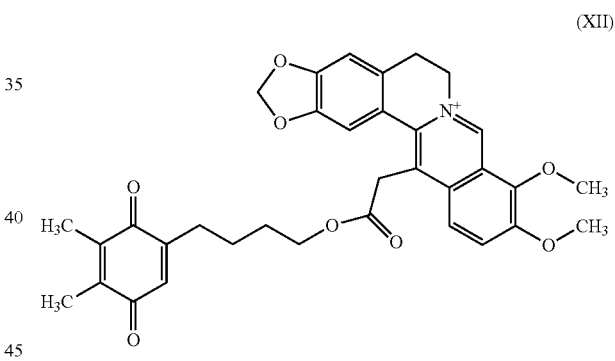

(XI)

and the reduced (quinone) form thereof.

In another aspect, the disclosure provides a compound of Formula XII:

(XII)

and the reduced (quinone) form thereof.

In yet another aspect, the disclosure provides a compound of Formula XIII:

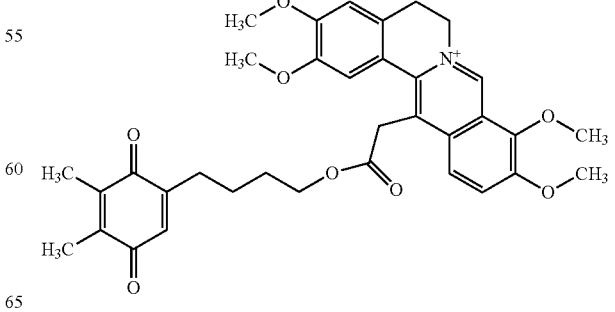

(XIII)

and the reduced (quinone) form thereof.

In another aspect, the disclosure provides a method of synthesizing the compound of Formula I according to claim 1. In this method 2,3-dimethylphenol is oxidized to 2,3-dimethyl-1,4-benzoquinone; 11-bromo-undecanoic acid is linked to triphenylphosphine to form 10-carboxy-decyl) triphenylphosphine; and 10-carboxy-decyl)triphenylphosphine is reacted with 2,3-dimethyl-1,4-benzoquinone in the presence of silver nitrate and ammonium persulfate to form the compound of Formula I in both reduced and oxidized forms.

In some embodiments, composition comprises about 70% to about 100% of the oxidized form, about 80% to about 100% of the oxidized form, about 90% to about 100% of the oxidized form, or about 95% to about 100% of the oxidized form.

In another aspect, the disclosure provides a method of purifying the compound of Formula I. In this method a preparation comprising the compound of Formula I is subjected to reversed-phase, gradient chromatography in a salt-free, unbuffered mobile phase system, to obtain a composition comprising at least 80% compound of Formula I in both oxidized and reduced forms. The mobile phase system comprises a first water-alcohol solution and a second water-alcohol solution, the first and second solutions containing different percentages of alcohol.

In some embodiments the gradient formed from the first and second water-alcohol solutions is about 1% alcohol to about 100% alcohol. In other embodiments, the water-alcohol solutions comprise ethanol, methanol, isopropanol, or propanol. In certain embodiments, the first solution comprises about 1% to about 30% ethanol, and the second solution comprises about 15% to about 100% ethanol. In one embodiment, the first solution comprises about 15% ethanol, and the second solution comprises about 40% ethanol, and about 95% of the compound of formula I purified is in the oxidized form. In other embodiments, the first solution comprises about 1% to about 20% isopropanol, methanol, or propanol, and the second solution comprises about 10% to about 100% isopropanol, methanol, or propanol. In a certain embodiment, the first solution comprises about 8% isopropanol, and the second solution comprises about 30% isopropanol.

In some embodiments, NaBr is added to the preparation comprising the compound of Formula I before chromatography such that the preparation comprises about 5 mM to about 10 mM NaBr. In some embodiments, the chromatography is performed at 5° C.

The disclosure also provides a method of purifying a composition of Formula I, comprising: subjecting a preparation comprising the compound of Formula I to gel filtration chromatography using 100% ethanol to obtain at least 85% pure compound of Formula I. In one embodiment, the preparation comprising the compound of Formula I is subjected to gel filtration chromatography using 100% ethanol to obtain at least 85% to 100%, about 90% to 95%, about 93% to 95%, at least 86%; at least 87%, at least 88%, at least 89% at least 90%, at least 91%, at least 92%, at least 93% at; least 94%, at least 95%, at least 96% at least 97%, at least 98%, or at least 99% of the compound of Formula I purified is in oxidized form. In one embodiment, the gel used is Sephadex LH-20-100 pre-equilibrated with 100% ethanol.

In another aspect, the invention provides a method of separating and purifying the oxidized form of a compound of Formula I from a preparation comprising both the oxidized and reduced forms of the compound of Formula I. In this method the preparation is contacted with a molecular trap in a solvent, the molecular trap comprising a carbonyl-containing agent and the molecular trap extracting the reduced form of the compound of Formula I from the preparation. The solvent containing the molecular trap and the extracted reduced form of the composition is then separated from the rest of the preparation, including the oxidized form.

In some embodiments, the carbonyl-containing agent is acetone, methylketone, acetophenone, or cyclohexanone. In certain embodiments, the solvent is hexane or heptane. In some embodiments, the content of the molecular trap in the solvent is about 0.5% to about 10%, about 1% to about 5%, about 1.5% to about 3.5%, or about 2.5%.

In some embodiments, the method further comprises removing the solvent from the composition by evaporation to form a concentrated composition comprising the reduced form of the compound of formula I. In other embodiments, the method further comprises purifying the reduced form of the compound of Formula I from the concentrated composition by gel filtration chromatography using 100% ethanol. In some embodiments, the method further comprises: removing the molecular trap from the composition by evaporation, to form a concentrated composition comprising the oxidized form of the compound of formula I; and purifying the oxidized form of the compound of Formula I from the concentrated composition by gel filtration chromatography using 100% ethanol. In some embodiments, the method further comprises repeating the removing and purifying steps to obtain a composition comprising at least 98% or at least 99% of the oxidized form, or of the reduced form, of the compound of Formula I.

In yet another aspect, the disclosure provides a molecular trap for separating the oxidized form of a compound of Formula I from the reduced form of the compound of Formula I. The trap comprises a carbonyl-containing agent dissolved in a hexane solvent or in a heptane solvent, wherein the carbonyl-containing agent comprises 2.5% vol/vol of the molecular trap.

BRIEF DESCRIPTION OF FIGURES

The foregoing and other objects of the present disclosure, the various features thereof, as well as the disclosure itself may be more fully understood from the following description, when read together with the accompanying drawings in which.

DESCRIPTION

Figure 1A:
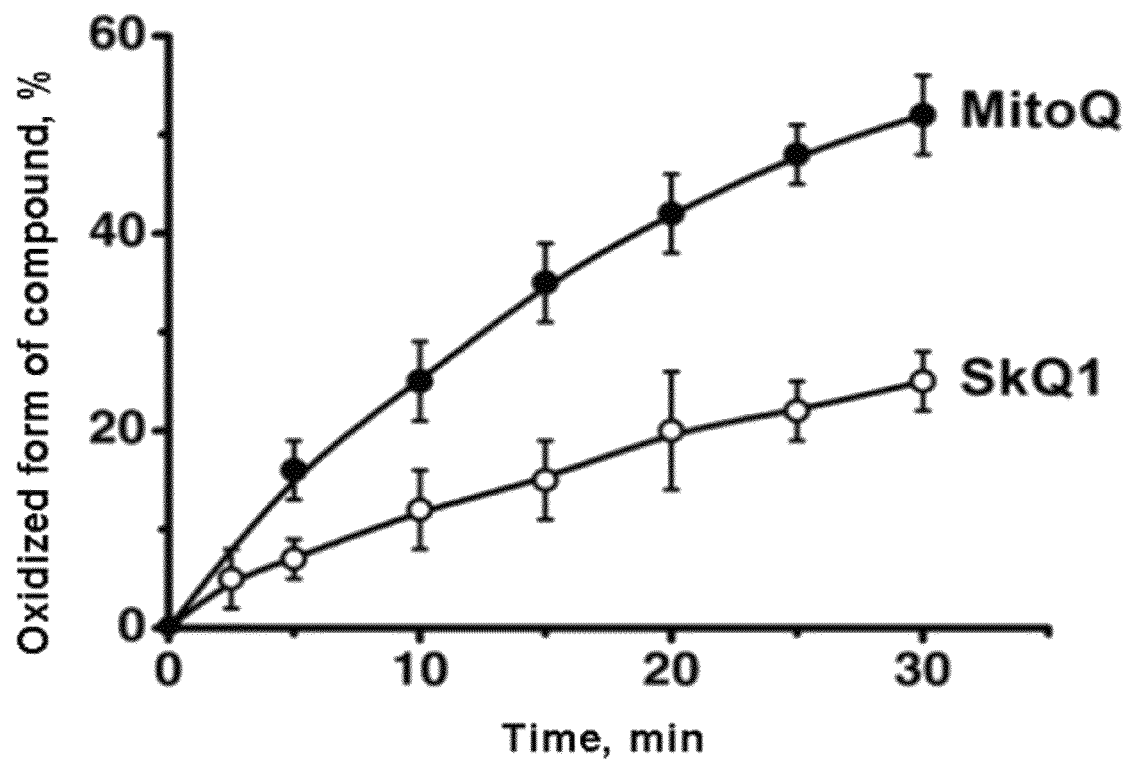
FIGS. 1A and 1B are graphic representations of the ability of compounds of general formula (I) (MitoQ and SkQ1) to be oxidized by oxygen (FIG. 1A) or superoxide (FIG. 1B) formed by the reaction of xanthine oxidase with xanthine.

The disclosures of these patents, patent applications, and publications in their entireties are hereby incorporated by reference into this application in order to more fully describe the state of the art as known to those skilled therein as of the date of the invention described and claimed herein. The instant disclosure will govern in the instance that there is any inconsistency between the patents, patent applications, and publications and this disclosure.

Unless defined otherwise, all technical and scientific terms used herein have the same meaning as commonly understood by one of ordinary skill in the art to which this disclosure disclosure belongs. The initial definition provided for a group or term herein applies to that group or term throughout the present specification individually or as part of another group, unless otherwise indicated.

1. Mitochondria-Addressed Antioxidants

Mitochondria-addressed antioxidants (MAA) are compounds which are targeted to, and which accumulate in mitochondria, and which possess antioxidant activity.

Aspects of the present invention are devoted to the production of pharmaceutical substances related to MAAs, and to the design and selection of specific MAAs which best correspond to relevant clinical tasks. In particular, the invention relates to MAA compounds comprising an antioxidant that is attached through a linker group to a lipophilic cation ("Skulachev-ion"). These MAAs are described by general formula (I) given below:

(I)

wherein:
A is effector moiety;
L is a linker group;
n is an integer from 1 to 20; and
B is a targeting group that provides targeted delivery of the compound into mitochondria.

A may be an antioxidant of general formula (II)

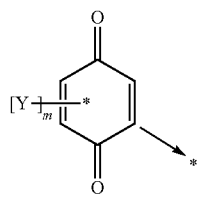
(II)

and/or reduced form thereof, wherein:
m is an integer from 1 to 3;
Y is an identical or different substituents selected from lower alkyl or lower alkoxy; or two vicinal Y are connected to each other so that they form a structure (III):

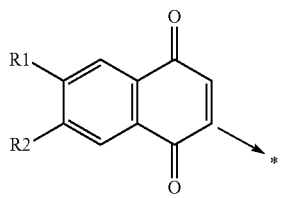
(III)

and/or reduced form thereof, wherein:
R₁ and R₂ are identical or different substituents selected from lower alkyl or lower alkoxy;

In some embodiments, L is a linker group, comprising:
a) a straight or branched hydrocarbon chain optionally containing one or more double or triple bond, or ether bond, or ester bond, or C—S, or S—S, or peptide bond; and which is optionally substituted by one or more alkyl, alkoxy, halogen, keto group, or amino group; or
b) a natural isoprene chain;

In some embodiments, B is a targeting group comprising:
a) a Skulachev-ion Sk:

wherein Sk is a lipophilic cation; and
Z is a pharmaceutically acceptable anion;
b) a amphiphilic zwitterion which is able to penetrate into mitochondria in its cationic form; or
c) Sk⁺ as a component of B is a lipophilic metal-organic compound, such as lipophilic metalloporphyrin having a structure:

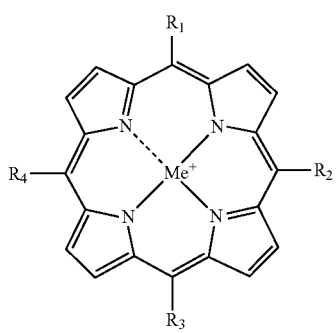

included in the composition of a compound of formula (I) through the moieties designated $R_1$, $R_2$, $R_3$ or $R_4$ which may be selected in accordance with required properties of the compound, for example, to increase or decrease hydrophobicity of the molecule.

$Me^+$ denotes a metal ion selected from Mn, Fe, Co, Cu, Mg or Zn.

Examples of structures of biologically active compounds belonging to MAAs of general formula (I) are shown in a scheme below.

SkQ1 (plastoquinonyl-decyl-triphenylphosphonium (PDTP) bromide)

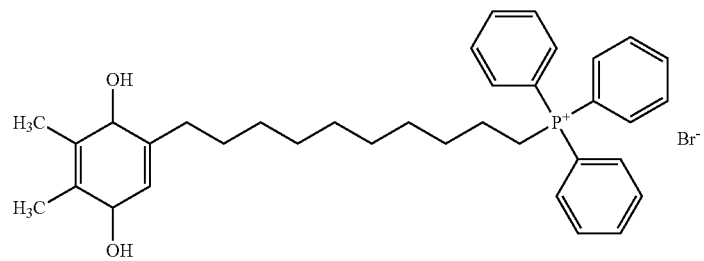

MitoQ

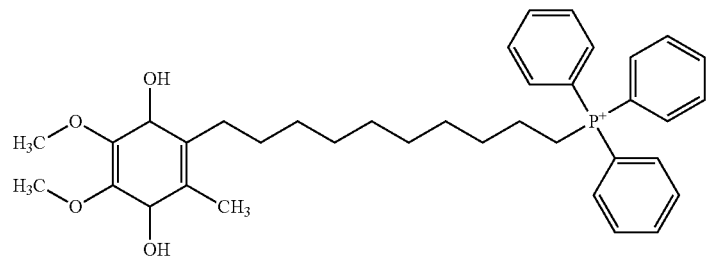

DMMQ

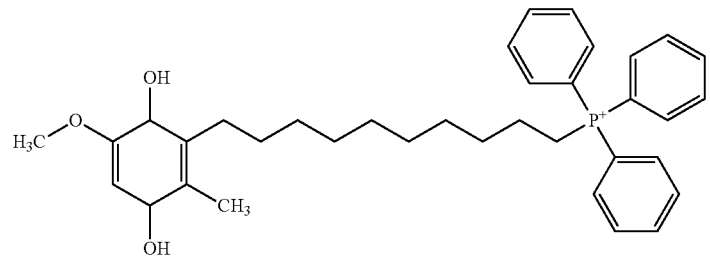

SkQR1

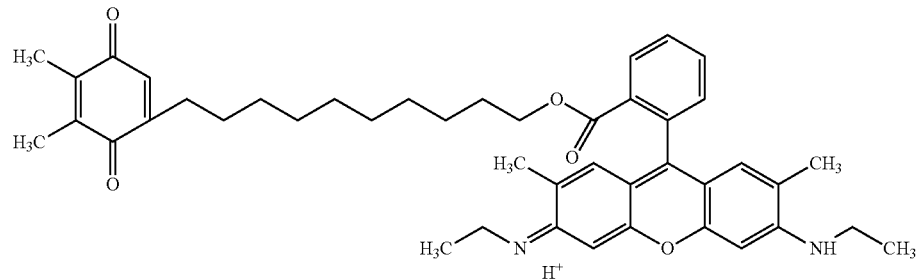

In some embodiments, compounds of formula (I) have pro-oxidants as effector moiety A. In a particular embodiment, desmethoxyubiquinone or ionol is used as the effector moiety as described by the following structures:

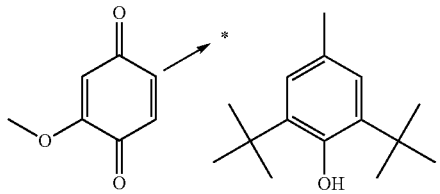

The corresponding compounds of formula (I) are mitochondria-addressed pro-oxidants.

Another aspect of the present invention is a method of designing and/or selecting a specific mitochondria-addressed compound.

2. Method of Designing New Mitochondrial Antioxidants

The study of chemical, physicochemical and biological properties of mitochondrial antioxidants to propose a new approach for design of compounds belonging to a class of compounds (I). Using the proposed model it is possible to design a structure of new mitochondria-addressed antioxidants with predetermined properties.

The design model of the new mitochondrial-addressed antioxidants is shown in a scheme below:

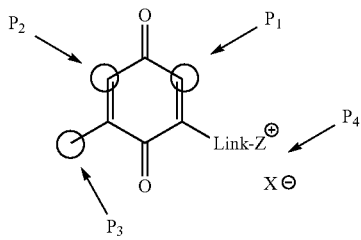

wherein:

P1 is a position that is responsible for stability and biological activity of a compound. If this carbon atom has no substituent, such a substance is maximally efficient as an antioxidant but relatively unstable. SkQ1, which is a 10 times more potent antioxidant than MitoQ, is an example. However, the presence of a methyl group at position P1 in MitoQ makes it more stable than SkQ1. The composition of the linker, 'Link', can also affect the stability of a substance. For example, the stability of a substance can be changed with the introduction of an ester bond, peptide bond, sulfide group, or other reactive groups to the 'Link'.

Positions P2 and P3 are responsible for regulation of the interaction with the mitochondrial respiratory chain. If one of these carbon atoms has no substituent, such a substance cannot be reduced by the mitochondrial respiratory chain which converts the compound into a pro-oxidant. The same effect can be achieved if the structure of one or both of the substituents at this position does not allow the respiratory chain to reduce and/or oxidize a corresponding compound.

Substituents at the same positions P2 and P3 may affect the ratio between pro-oxidant and antioxidant properties of the compound. The presence of oxygen atoms at positions P2 and P3 may lead to the formation of an internal hydrogen bond with the hydrogen atom of OH group of quinol in the reduced or partially reduced (quinol or semiquinone) forms of an antioxidant. Such a hydrogen bond may hinder the oxidation of the OH group in the reaction with free radicals and reactive oxygen species that drastically reduces the antioxidant properties of a substance compared to a compound in which there are no oxygen atoms at positions P2 and P3 (for example, when there are methyl groups). This may explain the difference between the properties of SkQ1 and MitoQ.

P4 is a position that is responsible for the penetrating ability of a biologically active substance. The ability to penetrate into mitochondria depends on charge and hydrophobicity of a compound. For example, experiments on artificial membranes show that compounds with triphenylphosphonium at position P4 are less penetrating than substances where at that position there is more hydrophobic cation-rhodamine G moiety.

Figure 2A:
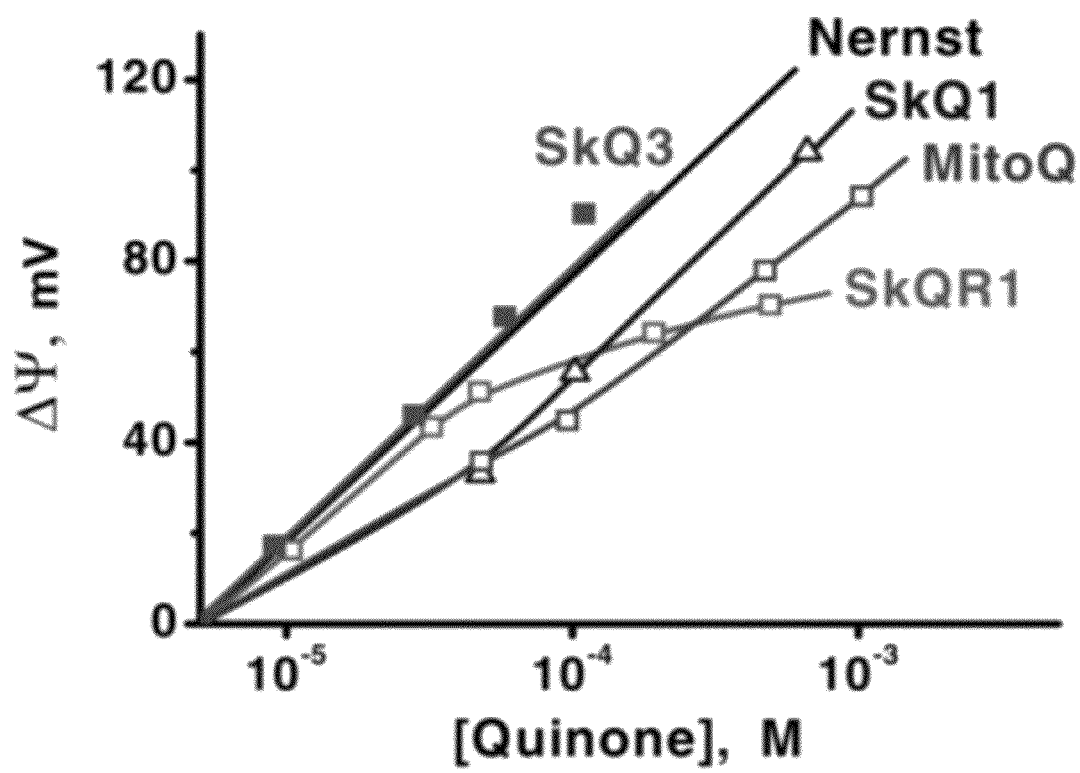
FIG. 2A is a graphic representation showing the ability of compounds of structure (I) (SkQ1, SkQR1, SkQ3), and MitoQ, to pass through the bilayer membrane and form a membrane potential ($\Delta\Psi$), compared to ideally penetrating monocation according to the Nernst equation (black line).
Figure 2B:
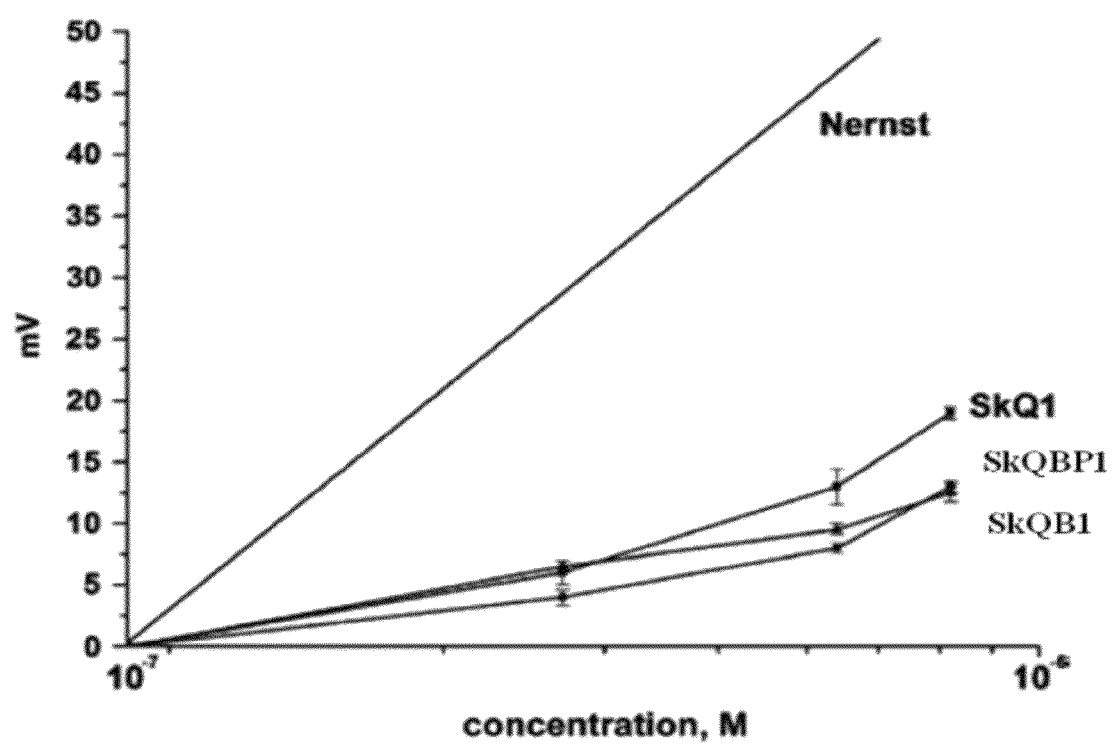
FIG. 2B is a graphic representation of the generation of transmembrane electric potential difference across a bilayer lipid membrane with SkQ1, SkQB1, and SkQBP1, where two compartments of the experimental chamber separated by a membrane (formed on an aperture in a Teflon septum) initially contained equal concentrations ($10^{-7}$ M) of the studied cation: SkQB1 (-•-), SkQBP1 (-▲-) and SkQ1 (-■-).

'Link' is the structural element that is also able to dramatically affect the properties of the compound. The length and composition of the 'Link' may affect the penetrating ability of the compound (FIGS. 2A and 2B). Reducing the length of the linker and increasing its hydrophilicity will reduce the penetrating ability of the compound. Also, by modifying the composition of the 'Link' one can change the stability of the compound. Introducing ester bonds, peptide bonds, other bonds which are less stable than the C—C bond into the linker can make the compound vulnerable for cellular enzymes such as esterases, or peptidases. Also changing the length of this element changes the position of the hydrophobic part of the molecule (antioxidant moiety) within the bilayer membrane that is an important factor in determining a possibility of interaction of the compound with the mitochondrial respiratory chain.

Thus, one aspect of the present invention relates to a method for designing and creating structures of mitochondria-addressed compounds with predicted biological activity. The "biological activity" is defined as the influence on biological systems and their models (i.e., artificial cell-free systems, subcellular fractions and organelles, cells, regions of tissues and organs or whole organism), that comprises the antioxidant effect, pro-oxidant effect, uncoupling effect on mitochondria, a change in the properties of biological membranes, and/or regulatory effect through different messengers at different levels (e.g., regulation of gene expression, of protein activity, of a hormonal profile of an organism, etc.).

3. Method of Designing MAA Compounds Using Combinatorial Libraries

Another aspect of the present invention relates to a combinatorial library of mitochondria-addressed compounds and methods for search and selection of promising compounds from this library. This library is a set of compounds of general formula (I) which are able to targetedly accumulate into mitochondria. The compounds for the library may be synthesized include, a lipophilic cation connected to a linker (or part of the linker) bearing an 'activated' residue, for example, a halogen through which the attachment of a variable part of the compound occurs. In other words, the library of mitochondria-addressed compounds can be obtained by attaching non-addressed, low molecular weight compounds to the lipophilic cation of the library.

The present invention also relates to a method of testing for the biological activity of compounds of the library in order to select compounds with desired activity. This testing may be automated or semi-automated. The method comprises the following steps: (1) testing that allows for the selection of a group of candidate substances from the library; (2) construction of a combinatorial sublibrary based on the selected substances and their modifications, if any; (3) testing the sublibrary to select compounds with the most pronounced, desired biological activity; and (4) repetition of steps 1 to 3 until all possible variants of the compounds are tried or until the desired biological activity is achieved.

A combination of several methods for testing the biological activity at steps 1 and 3 (above) which can significantly reduce the probability of artifact results is effective. The specific test methods can be adapted by qualified experts in the field of biochemistry, biophysics, bioenergetics, microbiology, molecular biology, cell biology or other fields of modern biology on the basis of publicly available literature data on the methods of work with combinatorial libraries and methods listed in the description of the invention. The examples below provide methods for testing the activity of mitochondria-addressed compounds in individual test tubes and can be easily adapted for testing combinatorial libraries by highly-productive methods using standard approaches.

4. Test Methods

Another aspect of the present invention is a set of test methods used to analyze the biological activity of new, mitochondria-addressed compounds of general formula (I). The new test compounds can be studied both individually and as part of combinatorial libraries. The set of test methods comprises the following methods:

1) testing redox properties and stability of the mitochondria-addressed compounds of general formula (I) in vitro;
2) testing the penetrating ability of the mitochondria-addressed compounds of general formula (I) on artificial black membranes;
3) testing the protective or damaging effect of the mitochondria-addressed compounds of general formula (I) on membrane proteins using model artificial membranes containing gramicidin channels;
4) testing the antioxidant or pro-oxidant effect of the mitochondria-addressed compounds of general formula (I) on isolated mitochondria;
5) testing the antioxidant or pro-oxidant action of the mitochondria-addressed compounds of general formula (I) in animal, plant, bacterial or yeast cell cultures;
6) testing the anti-apoptotic, anti-necrotic, pro-apoptotic, pro-necrotic activity of the mitochondria-addressed compounds of general formula (I) in cell cultures;
7) testing for the accumulation of the mitochondria-addressed compounds of general formula (I) in cells;
8) testing the specific activity of the mitochondria-addressed compounds of general formula (I), the "specific activity" being defined as the ability to activate or suppress certain metabolic pathways that in turn may be manifested in the activation of certain genes at the transcriptional level, in mRNA stability or translation; at the level of protein modifications; comprising phosphorylation, dephosphorylation, proteolysis, glycosylation, carbonylation, and other ways of changing the activity of proteins or protein complexes; activation or inhibition of metabolic pathways manifested in change of other physiological parameters of cells such as: change in the respiratory rate, in the rate of production of certain metabolites, in the rate of consumption of certain substrates, in membrane potential, or in ionic conductivity of the outer membrane, the mitochondrial membrane, on membranes of other organelles, change in concentrations of certain ions including change in pH in cellular cytoplasm or in other cellular compartments, change in intracellular transport of biomolecules, vesicles and organelles, change during the cell cycle, change that leads to cell division, cell transformation, or cell death, or, conversely, change that leads to their survival; and/or
9) testing the biological activity of the mitochondria-addressed compounds of general formula (I) in vivo in animals or plants to be applied at later steps of testing.

Thus, this aspect relates to each of the above tests separately and in combinations to study the properties of new compounds of general formula (I), and to forecast the prospects for practical use of these compounds in medicine, biotechnology, and cosmetology.

5. Methods for Interpretation of Results

Another aspect is a method for the interpretation of results obtained during testing the compounds of general formula (I) in order to forecast the prospects of practical use of candidate compounds in medicine, biotechnology, and/or cosmetology, and in order to select the most promising compounds.

The basic element of the method is the comparison of the activity of the candidate compounds with the activity of compound SkQ1. The results of tests of SkQ1 activity are presented in the Examples below.

Thus, SkQ1 data may be considered as the starting point, the fixed point, and/or the standard for predicting the effectiveness of other compounds of general formula (I), since SkQ1 is a quite effective biologically active compound and can be applied in medicine, biotechnology, and cosmetology (see, e.g., PCT/RU2006/000394, PCT/RU2006/000546, PCT/RU2006/000547).

It is preferable if test compound can be reduced by the mitochondrial respiratory chain, with the enzymes and co-enzymes of the respiratory chain. Depending on concentration MAA can exhibit antioxidant or pro-oxidant properties. It is important feature of test compound that its antioxidant properties overcome pro-oxidant properties.

Compounds MitoVitE, DMMQ, and MitoQ have less pronounced antioxidant properties. Thus they can serve as "negative" fixed points in the process of selection of the most promising compounds. Test compounds which have properties similar to MitoVitE, DMMQ, or MitoQ should be avoided.

Upon selection of new compounds based on their properties, compounds are selected which have activity closer to SkQ1 than to MitoQ. The "activity" is defined as the ability to show antioxidant properties at low and ultra-low concentrations. MAAs with increasing doses have a strong pro-oxidative effect on various biological objects (see EXAMPLES below, and Doughan et al. (2007) *Antioxid. Redox Signal.* 9:1825-36). At lower doses, these compounds exhibit antioxidant properties.

Thus, a characteristic of the mitochondria-addressed pharmaceutical substance is the so-called "the window of application," i.e., the difference between the minimum concentration (dose) of a substance that already displays antioxidant properties, and the minimum concentration (dose) of a substance manifesting pro-oxidant properties. Exceeding the latter concentration (dose) is undesirable in practical application of the substance and may significantly limit the possibility of such an application. Methods for assessing the window of application at different levels are given below in the Examples. A pair of compounds, SkQ1 and MitoQ, can serve as a good fixed points for assessing the prospects of the test compounds, since SkQ1 has a sufficient 'window of application', while MitoQ does not.

The method for interpretation of the results of the tested compounds is given below.

On the basis of the properties of the substances tested in vitro (tests 1, 2, and 3 described in the Test Methods section above) the antioxidant and pro-oxidant properties of test compounds can be estimated. This allows the prediction of their applicability in the fields where the use of an antioxidant or pro-oxidant is useful. In vitro tests also allow the determination of the ability of candidate compounds to penetrate through biological membranes and thus to predict bioavailability of the compounds, their ability to overcome various barriers in an organism (e.g., blood-brain barrier), as well as their stability.

Examples of interpretations of test results which are an aspect of the present invention, are given below in the Examples. Using these interpretations, a qualified expert in the field of biochemistry, biophysics, bioenergetics, microbiology, molecular biology, cell biology or other fields of modern biology can correctly assess the results of testing candidate compounds and select the most promising and the most suitable compounds for the required practical application.

To confirm the feasibility of the present invention and the correctness of the proposed model, new mitochondria-addressed antioxidants SkQ3, SkQ4, SkQ5 and SkQB1 have been synthesized and tested. Their structures are below.

SkQ3:

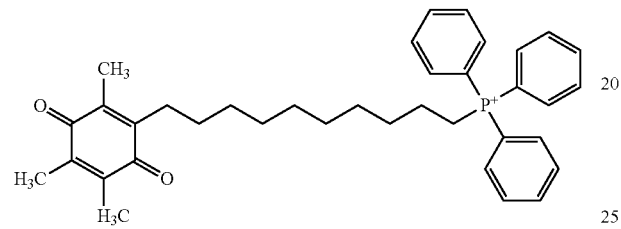

The predicted specifications of SkQ3 are that the compound must be more stable but have less pronounced antioxidant properties than SkQ1. The compound can be used in plant biotechnology, mycology, and microbiology.

SkQ4:

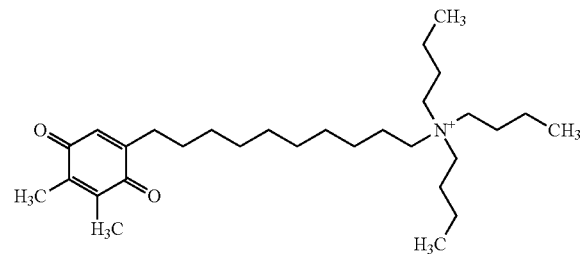

The specifications of SkQ4 include a lower ability to penetrate through biomembranes than SkQ1. Thus, the bioavailability of the preparation and severity of side effects must be reduced.

SkQ5:

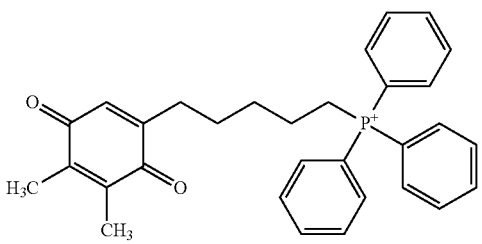

The specifications of SkQ5 include a decrease in the length of the linker between "Skulachev-ion" and the antioxidant, which reduces the hydrophobicity of the compound, and can affect the rate of penetration of the compound through the membranes.

A series of SkQB compounds with enhanced penetrating ability as compared to SkQ1 comprises all the compounds in which a natural compounds (for example, berberine and palmatine) is used as the "Skulachev-ion." Compounds of the SkQB series (e.g., SkQB1 whose formula is given below) have enhanced penetrating ability and therefore have a greater ability to overcome the blood-brain barrier and blood-ophthalmic barrier. Also, compounds of the SkQB series may have less severe side effects, since berberine (as well as palmatine) are natural compounds of plant origin.

SkQB1A:

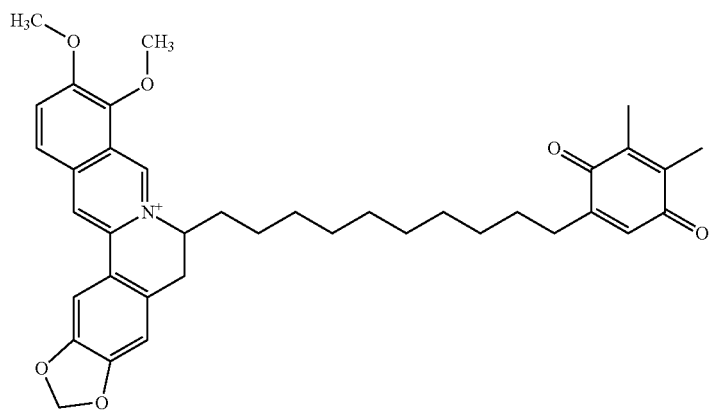

SkQB1B:

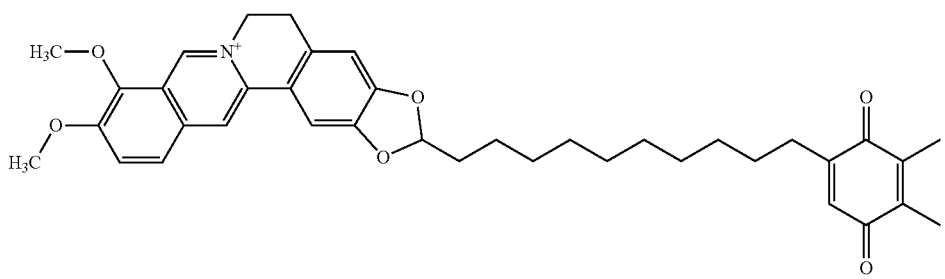

SkQB based on berberine may be represented by general formula:

SkQB:

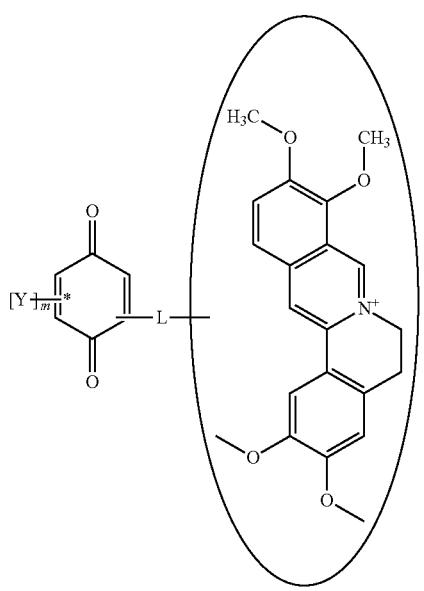

wherein:

m is an integer from 0 to 3 (such as 2, i.e., the left side of the formula is plastoquinone moiety), 'L'—linker that has the length from 1 to 50 units comprising:

1) straight or branched hydrocarbon chain optionally containing one or more double or triple bond, or ether bond, or ester bond, or C—S, or S—S, or peptide bond, and which is optionally substituted by one or more substituents selected from alkyl, alkoxy, halogen, keto group, amino group; or
2) a natural isoprene chain.

As a variant, "L" is decane moiety. The right side of the compound formula is berberine moiety attached to linker 'L' through one of its constituent atoms. The attachment can be made through C—C, C—O, C—N, C—S bonds including ester bond, peptide bond, disulfide bond. Including the attachment can be made through ether bond by displacing one of the methoxy groups of berberine.

In compounds of the SkQB series, palmatine may be used in place of berberine. Other compounds based on berberine and palmatine are the following:

SkQB1:

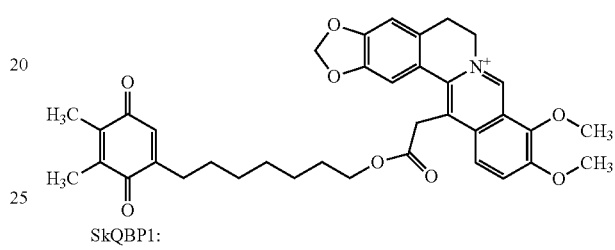

SkQBP1:

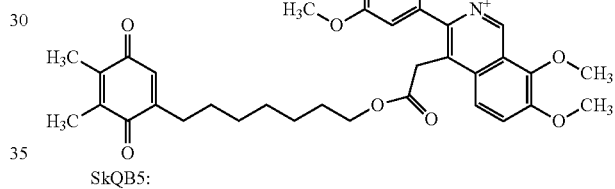

SkQB5:

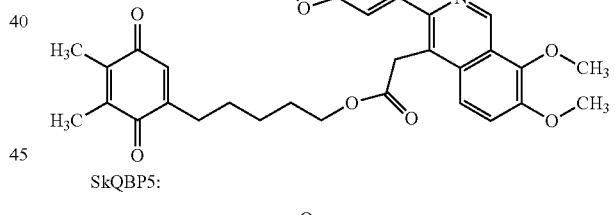

SkQBP5:

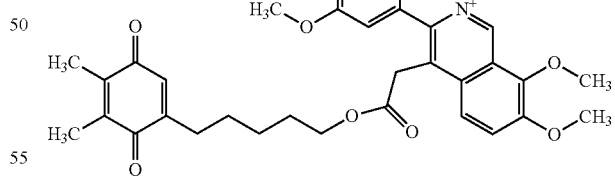

Methods of synthesis and description of the chemical properties and biological activity of the above compounds are given below in the Examples.

6. MAA-Based Pharmaceutical Substances

One aspect of the present invention are parameters of regulatory documents which allow the use of MAA-based pharmaceutical substances in medical practice.

A "pharmaceutical substance" is a substance which is prepared for use as ingredient of a medicinal preparation and meets the pharmacopoeia requirements.

The parameters according to the disclosure comprise the following indicators: (1) authenticity determined in particular by means of (a) spectrophotometry at a given wavelength range and comparison with the results of a spectrophotometric study of the MAA sample; (b) IR spectroscopy of a substance taken by the method of Frustrated Total Internal Reflection which has coincidence of the absorption bands with the absorption bands of the included spectrum in position and intensity of the bands; and (c) reaction to bromides where the chloroform layer turns yellow; (2) impurity content determined by the HPLC method where the content of each individual impurity does not exceed 1.5%, and the total impurity content does not exceed 4.0%; (3) heavy metal content which does not exceed 0.001%; (4) a residual organic solvent content (such solvents as ethanol, methanol and chloroform); (5) sterility; (6) quantification of the substance; (7) packaging, labeling, and storage; and (8) established expiration date.

Figure 12:
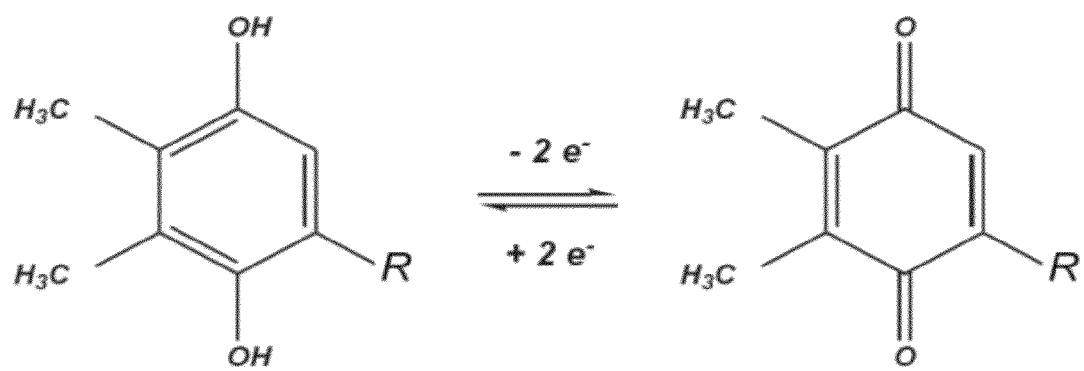
FIG. 12 is a schematic representation of the equilibrium of quinone and quinol forms of MAAs (R-linker group connected to lipophilic ion ("Skulachev-ion")).

In practice, the known quinone-containing mitochondria-addressed compounds, including SkQ1, SkQR1, MitoQ and others (see above), are mainly in the one oxidized (quinone) form. Under normal conditions, the oxidized form can be partially reduced to the quinol form (see FIG. 12). Thus, when using MAAs as pharmaceutical substances, the main impurity is the reduced form of the MAA whose content can reach 5% to 8% and/or more. Isolation and detailed study of this reduced form is a difficult task because of its high chemical lability and tendency to undergo complex redox transitions.

The production of a pharmaceutical substance containing an MAA in the quinone form free of the reduced (quinol) form by standard methods for chromatographic purification is difficult because of the similarity of these compounds.

Another problem encountered in the purification process of the above series of MAA preparations is the need to preserve a characteristic counterion, for example, a bromine ion. Usual conditions for ion exchange chromatography or for high performance liquid chromatography (HPLC) are too harsh with respect to the labile compounds and do not guarantee preservation of the counterion in the initial structure. Thus, existing methods and techniques for isolation and purification of preparations of an MAA series do not provide the necessary parameters of purity for pharmaceutical substances.

In the present invention this problem can be solved by two methods. In Method 1, non-standard HPLC in a salt-free, un-buffered, mobile phase system, is used, and at the final stage, gel-filtration of the highly concentrated solution of the preparation is performed. In Method 2, a "molecular trap" of the reduced form of MAA is used which takes the form of an agent in a nonpolar solvent. The agent which acts as an effective inducer of oxidation of the reduced form or it can serve as a competitive substituent of the quinone form in the quinone-quinol equilibrium. Thus, another aspect of the present invention is a method of producing MAA in a form suitable for pharmaceutical substances, comprising Method 1 and/or Method 2.

Another aspect of the present invention is an improved method for the synthesis of MAAs on the basis of quinones. The improved method allows for the industrial production (synthesis) of MAAs using cheaper and more available components. In particular, in the case of the synthesis of plastoquinonyl-decyl-triphenylphosphonium (PDTP) bromide and other derivatives of plastoquinone, 2,3-dimethylphenol rather than dimethyl hydroquinone can be used as initial reagent. The synthesis involves the following steps:
1. oxidation of 2,3-dimethylphenol (1) to 2,3-dimethyl-1,4-benzoquinone (2) with the Jones reagent;
2. attachment of 11-bromo-undecanoic acid (3) to triphenylphosphine with the formation of (10-carboxy-decyl)triphenylphosphine bromide (4); and
3. formation of the desired compound (5) by the reaction of the produced compound (4) with 2,3-dimethyl-1,4-benzoquinone (2) in the presence of silver nitrate and ammonium persulfate.

Figure 13:
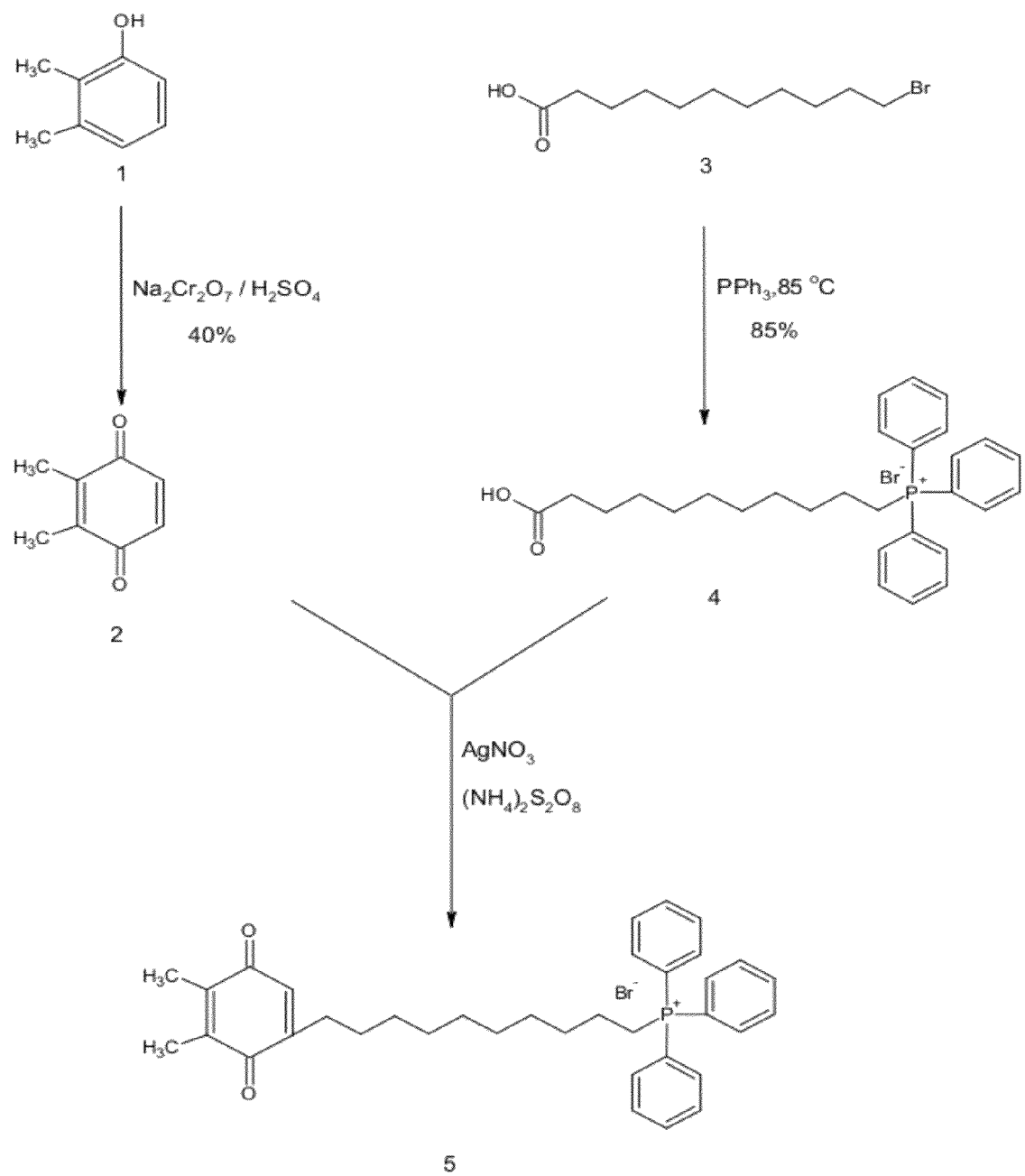
FIG. 13 is a schematic representation of the improved method of synthesis of the mitochondria-addressed antioxidant PDTP.

The general scheme of the synthesis is shown in FIG. 13, and is described in the Examples below.

The following are experimental examples intended to illustrate the possibility of applying the invention to the development of new mitochondria-addressed compounds. The results of experiments (tests) are also starting points for evaluating prospects for new compounds developed (or selected from combinatorial libraries) by experts in the field using the present invention to search for new mitochondria-addressed compounds. In this regard, experimental examples are called 'tests', since they are methods for testing new compounds.

EXAMPLES

Example 1

In Vitro Testing Redox Properties and Stability of Compounds of General Formula (I)

The first step in selection of compounds corresponding to structure (I) is testing their redox properties. Substances with predetermined pro-oxidant or antioxidant properties can be selected. To select compounds with potential antioxidant properties, their ability to be oxidized by oxygen or superoxide formed in the reaction of xanthine with xanthine oxidase is tested.

Stability of the reduced forms of SkQ1 and MitoQ over time was investigated by the analysis of absolute absorption spectra of the compounds in the range from 240 nm to 310 nm recorded using a double-beam Pye Unicam SP 1100 spectrometer (England). Quinone derivatives were reduced with sodium tetrahydroborate in a medium contained 20 mM MOPS-KOH, pH=7.6. A reference cuvette containing the reductant, and not containing SkQ1 or MitoQ, was added to both cuvettes, and measurements were made after the release of the hydrogen. The degree of reduction of quinones was assessed by the magnitude of the peak area by the weighing method. The absolute value of the absorption maximum at 267 nm was measured for comparison.

Figure 1B:
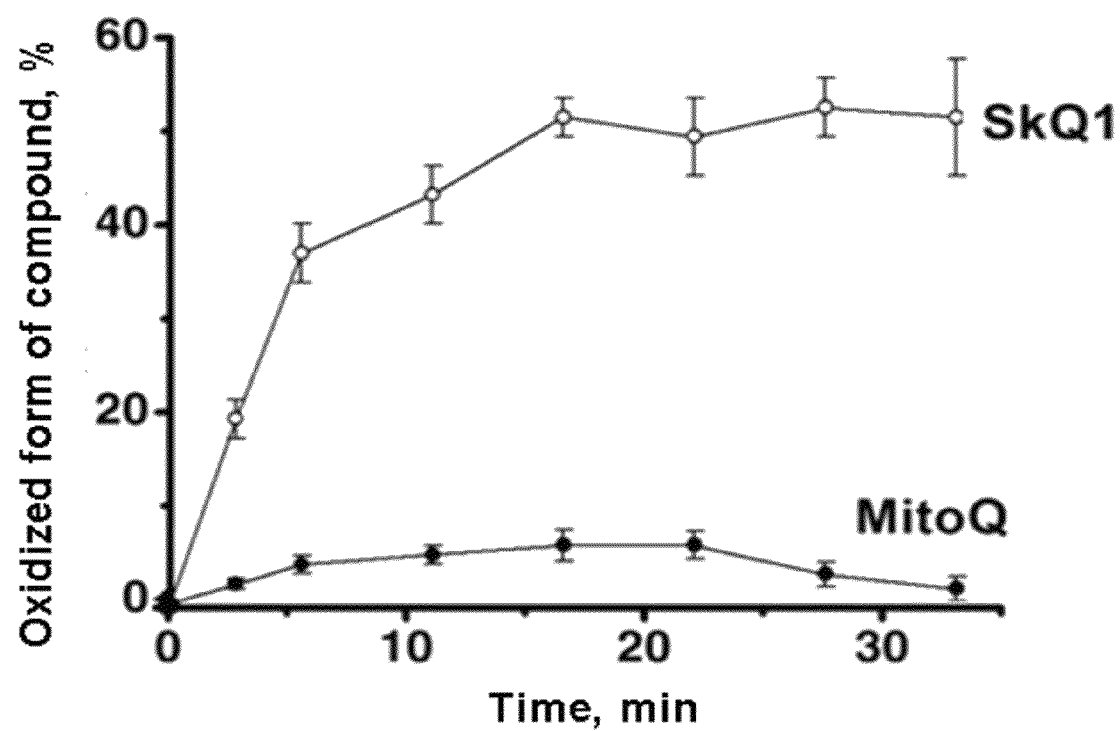

The results indicate that the reduced (quinol) form of SkQ1, when exposed to oxygen, is more resistant to oxidation by atmospheric oxygen than MitoQ (FIG. 1A). Thus, SkQ1 is less prone to interact spontaneously with oxygen and form radicals that potentially indicate it is less toxic for a cell. On the other hand, when the compounds were oxidized not by oxygen but by superoxide formed in the reaction of xanthine oxidase with xanthine, the oxidation of SkQ1 was much more effective than that of MitoQ (FIG. 1B). This may indicate that SkQ1 is more potent as an antioxidant, and that its reduced (active) form is more resistant to spontaneous oxidation by atmospheric oxygen as compared to MitoQ, and has a higher affinity for superoxide radical.

Example 2

Testing Penetrating Ability of Mitochondria-Addressed Compounds on Artificial Black Membranes To test the penetrating ability of mitochondria-addressed compounds of structure (I), a method is used based on the ability of ions to penetrate through the phospholipid membrane bilayer moving along the concentration gradient. The bilayer membrane separates two chambers filled with an aqueous solution, and the test substance is added to one of the chambers (Starkov et al. (1997) ibid.). If a charged substance can penetrate through the bilayer membrane, its rapid diffusion out of the chamber having a high concentration of the substance, to the chamber having a low concentration of the substance, occurs, and thus a membrane potential difference is created. For ions which are carrying one charge and able to easily penetrate through the membrane, a 10-fold concentration gradient allows for creation of a potential of 60 mV (according to the Nernst equation). This method was used in various studies of the ability of ions to pass through the lipid bilayer of the membrane.

Using this method, several substances of structure (I) (SkQ1, SkQ3, SkQR1 and MitoQ) were tested.

FIG. 2A shows that SkQ3 and SkQR1 fully obey the Nernst equation at concentrations ranging from $5 \times 10^{-6}$ M to $5 \times 10^{-4}$ M (for SkQ3) and from $5 \times 10^{-6}$ M to $5 \times 10^{-5}$ M (for SkQR1). At concentrations higher than $5 \times 10^{-5}$ M, SkQR1 ceases to obey the Nernst equation, probably due to its ability to damage the membrane at high concentrations. The SkQ1 and MitoQ gradient begins to create the potential in accordance with the Nernst equation at higher concentrations (ranging from $5 \times 10^{-5}$ M to $5 \times 10^{-4}$ M). Thus, on the basis of the data, it can be concluded that SkQ1 and MitoQ have less penetrating abilities compared to SkQ3 or SkQR1. This method is useful at the stage of primary selection of potential mitochondria-addressed compounds of structure (I), as it allows the quick selection of compounds which have the highest penetrating ability, and hence, i.e., are potentially more bioavailable.

The penetrating ability of compounds SkQB1 and SkQBP1 was also analyzed.

FIG. 2B shows the high penetrating ability of these compounds (their penetrating ability not being inferior to that of SkQ1).

SkQB1 and SkQBP1 were shown to generate membrane potential ($\Delta\psi$) of proper direction (compartment with lower cation was positively charged). Within the concentration range from $10^{-7}$ to $10^{-6}$ M, SkQB1 and SkQBP1 generated almost the same $\Delta\psi$ as SkQ1 (FIG. 14), indicating that permeabilities of membranes for these three compounds were similar. Theoretical (Nernstian) potential was not reached at such low concentrations of the cations. Further, increase in the concentrations was limited by poor solubility of SkQB1 and SkQBP1 in aqueous solutions.

Example 3

Testing Protective or Damaging Effect of Mitochondria-Addressed Compounds on Membrane Proteins Using Artificial Model Membranes Containing Gramicidin Channels A method was developed which allows the study of the antioxidant activity of compounds in a simple system consisting of a bilayer membrane, a conducting protein gramicidin and a photosensitizer (Mito Tracker Red, Invitrogen, Carlsbad, Calif.), thrice sulfonated aluminum phthalocyanine or zinc phthalocyanine). The method uses the ability of reactive oxygen species generated by photoactivation of the photosensitizer molecules to damage gramicidin channels, resulting in a sharp decrease in the conducting ability of the bilayer membrane. Apart from the photosensitizers, damage to gramicidin channels can be induced by initiating the Fenton reaction (the reaction of ferrous iron with $H_2O_2$ forming a highly reactive hydroxyl radical: ($Fe^{2+}+H_2O_2 \rightarrow Fe^{3+}+.OH+^-OH$), resulting in the formation of such highly reactive oxygen species as the hydroxyl radical. The Fenton reaction is initiated by a mixture of $FeSO_4$, ascorbate, and tert-butyl hydroperoxide. Compounds SkQ1, SkQ3 and MitoQ were tested using this method. The addition of ferrous sulfate in combination with potassium ascorbate to a medium containing mitochondria causes a reaction of ferrous iron with $H_2O_2$ (the Fenton reaction) to form the highly reactive hydroxyl radical ($Fe^{2+}+H_2O_2 \rightarrow Fe^{3+}.OH+^-OH$).

Figure 3A:
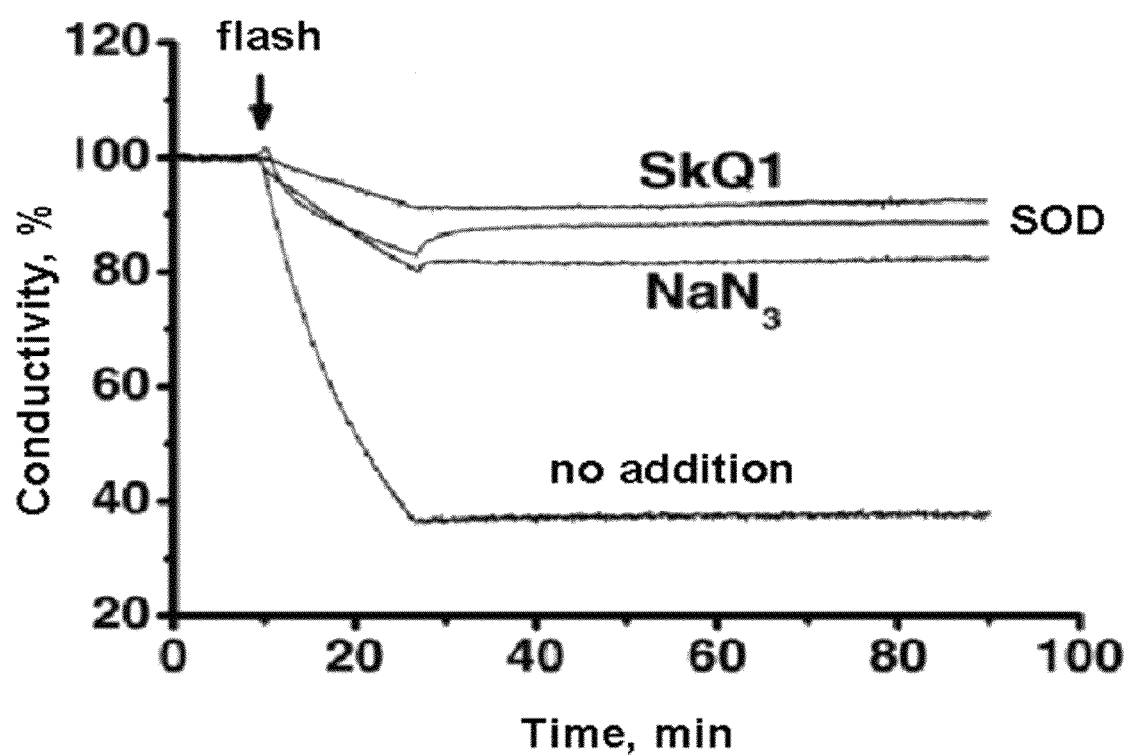
FIGS. 3A and 3B are graphic representations showing the protective or damaging effect (% conductivity) of mitochondria-addressed compounds on membrane proteins using artificial model membranes containing gramicidin channels, where damage to gramicidin channels was stimulated by photoactivation of phthalocyanine photosensitizer (FIG. 3A) or a mixture of FeSO₄, ascorbate and tert-butyl hydroperoxide (FIG. 3B).
Figure 3B:
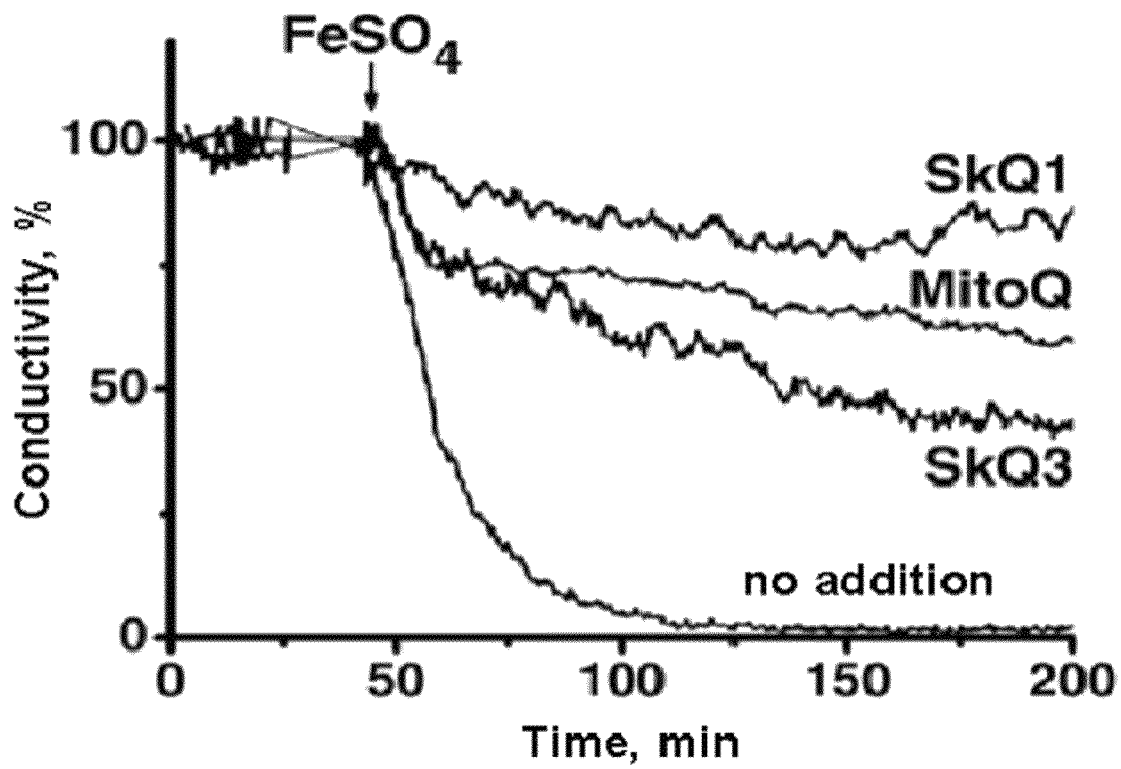

FIG. 3A shows that photoactivation of phthalocyanine by a short flash of light leads to a strong decrease in membrane conductance due to damage to gramicidin channels in the bilayer membrane. The fall in membrane conductance was effectively blocked by sodium azide (a highly efficient system to trap singlet oxygen), as well as by the enzyme superoxide dismutase (which catalyzes the conversion of superoxide into relatively low active hydrogen peroxide). Neither sodium azide nor superoxide dismutase completely prevents the fall in conductance of the bilayer membrane. This indicates that photoactivation of phthalocyanine is associated with the generation of both singlet oxygen and superoxide. In this model, SkQ1 was the most efficient, since SkQ1 is a broad-spectrum antioxidant that protects against various reactive oxygen species. In another model, where damage to gramicidin channels was stimulated by the mixture of $FeSO_4$, ascorbate, and tert-butyl hydroperoxide, SkQ1 was also the most efficient, while MitoQ and SkQ3 appeared to be less efficient antioxidants (FIG. 3B).

This method of testing the antioxidant capacity of the synthesized compounds is highly efficient, and allows not only for the evaluation of the antioxidant activity of the compounds, but also for the determination of the specificity of the compound for specific reactive oxygen species. As a reference substance for the method, SkQ1 is used as the most efficient compound because it exhibits the antioxidant activity towards a wide range of reactive oxygen species.

Example 4

Testing Antioxidant or Pro-Oxidant Effect of Mitochondria-Addressed Compounds on Isolated Mitochondria 1. Ability of Compounds of General Formula (I) to Accumulate in Mitochondria.

The ability of compounds of general formula (I) to accumulate in mitochondria was tested using a tetraphenylphosphonium-selective electrode. The method is used for compounds of general formula (I) in which the lipophilic cation tetraphenylphosphonium is used as the target group. With this electrode, it is possible to measure distribution of tetraphenylphosphonium cation (or compounds which comprise this cation) between the mitochondrial matrix and the medium.

Figure 4A:
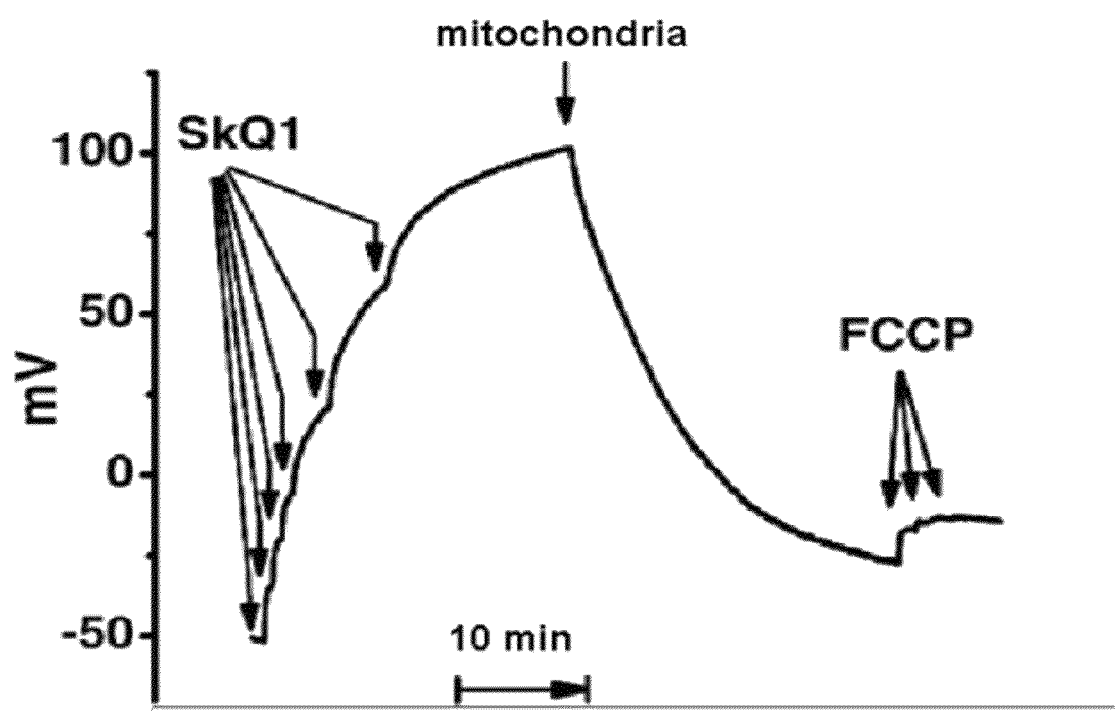
FIGS. 4A and 4B are graphic representations showing the accumulation of SkQ1 (FIG. 4A) and SkQ5 (FIG. 4B) in mitochondria measured (mV) with the use of the TPP⁺ electrode.
Figure 4B:
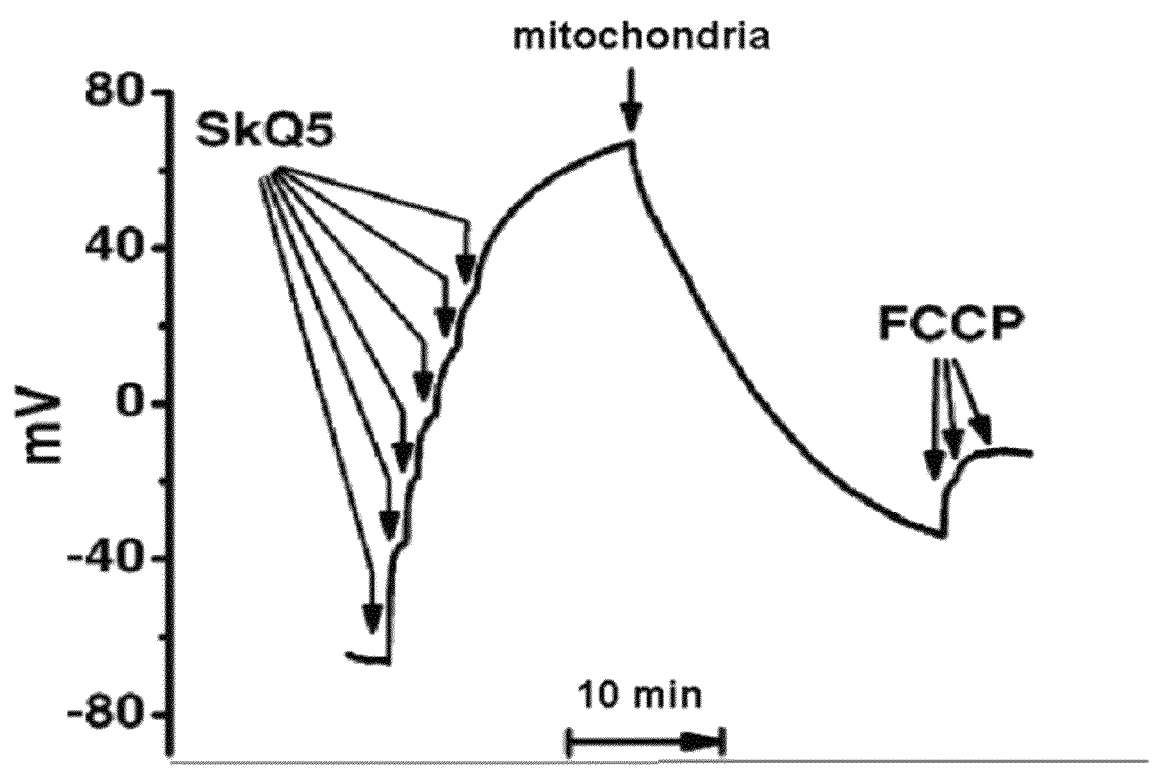

FIG. 4 shows that SkQ1 accumulates in mitochondria within 15 min to 20 min. The fall in mitochondrial membrane potential caused by oxidative phosphorylation uncoupler FCCP leads to release of a relatively small number of SkQ1 from mitochondria. Given that SkQ1 is a lipophilic cation (the octanol/water distribution ratio for SkQ1 is 20000/1), the main amount of SkQ1 accumulates in the mitochondrial membrane independent of the degree of energization of the mitochondria. If the less lipophilic SkQ5 is used in place of SkQ1, the level of energy-independent accumulation is reduced. This method allows the investigation of the efficiency of the accumulation of compounds of general formula (I) in mitochondria, the dependence of the rate of their accumulation on the functional state of mitochondria, as well as the prediction of the potential bioavailability of tested compounds.

2. Reduction of the Ability of Compounds of General Formula (I) by the Mitochondrial Respiratory Chain.

An advantage of mitochondria-addressed antioxidants of the present invention is their ability to be reduced by mitochondrial respiratory chain. To study the reduction of compounds of general formula (I) by mitochondrial respiratory chain, the rate of change in the ratio between the oxidized and reduced forms of the compounds was measured in the presence of respiratory substrates in an isolation medium of rat liver mitochondria. The measurements were performed in the presence of mitochondria.

Figure 5A:
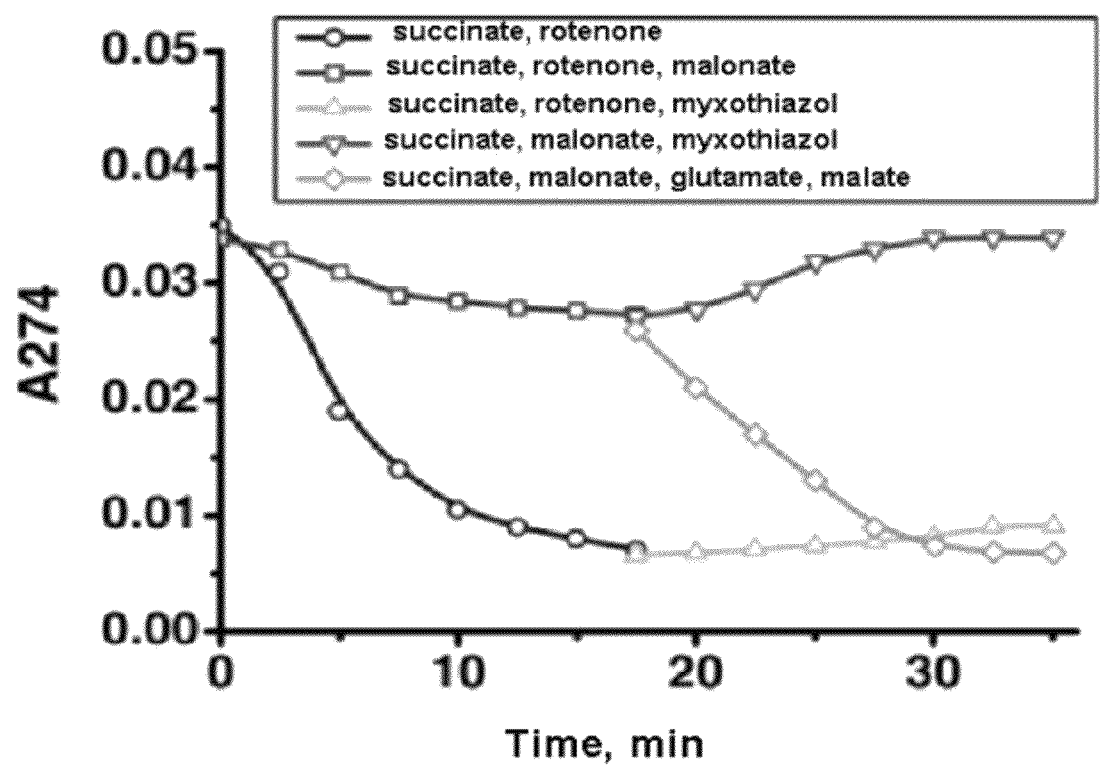
FIGS. 5A and 5B are graphic representations showing the ability of mitochondria to reduce or oxidize SkQ1 depending on the activity of the respiratory chain components shown by measuring $A_{274}$.
Figure 5B:
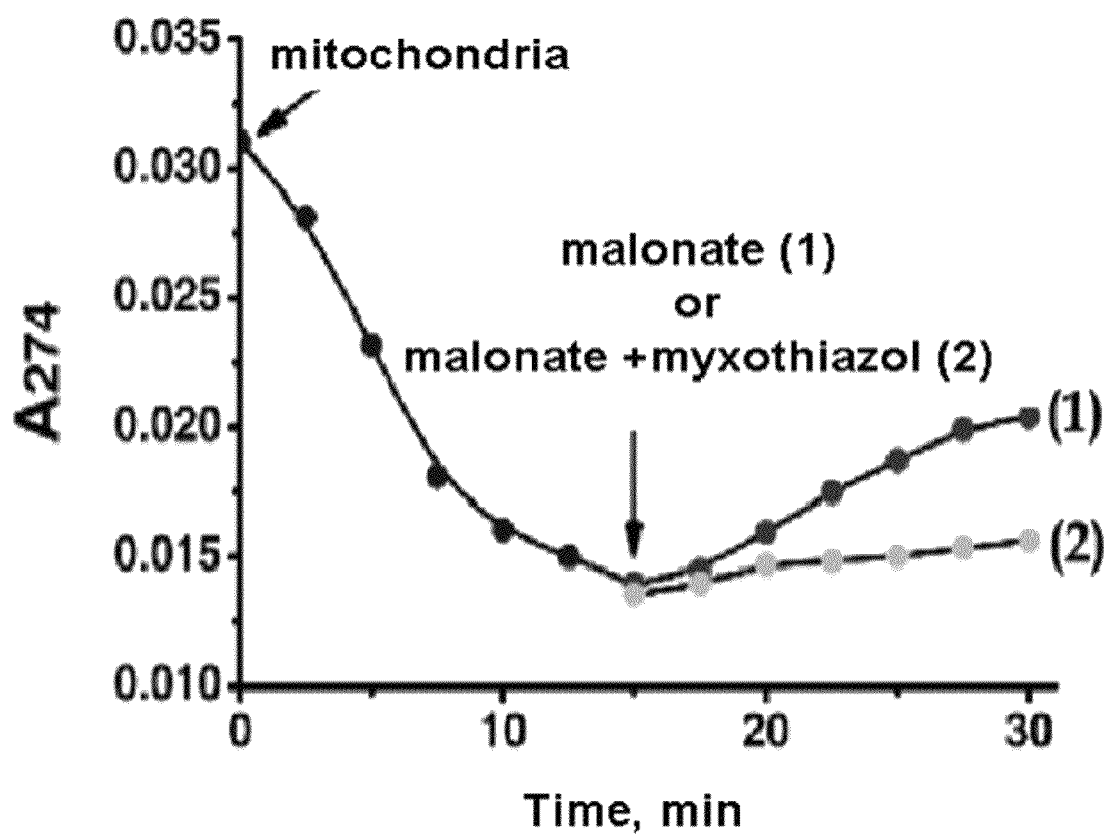

The experiments showed that SkQ1 can be reduced by the mitochondrial respiratory chain. The use of various substrates for oxidation showed that SkQ1 can be reduced with both complex I (mitochondria were energized with glutamate and malate) and complex II (substrate for oxidation was succinate) (FIG. 5A). To eliminate the influence of endogenous substrates, complex I inhibitor rotenone as well as complex II inhibitor malonate were used. Inhibition of complex II by malonate in the presence of rotenone stimulated oxidation of SkQ1, probably by complex III. Inhibition of complex III by myxothiazol, in turn, prevented oxidation, which confirms the ability of complex III to oxidize SkQ1 (FIG. 5B). Oxidation of SkQ1 with complex III is much slower than its reduction with complex I and complex II (FIG. 5B). These data indicate that in energized mitochondria, SkQ1 is mostly in the reduced state (quinol form) in which it manifests antioxidant properties.

Thus, this method allows for the study of the ability of compounds of general formula (I) to be reduced with mitochondrial respiratory chain. In addition, on the basis of the data, the prediction of pro-oxidant or antioxidant properties of test compounds can be made.

3. Antioxidant Activity of Compounds of General Formula (I) Under Conditions of Mitochondrial Oxidative Stress.

One of the most widely used methods for determination of oxidative stress in mitochondria, cell cultures, or tissues, is a method for quantitative determination of malondialdehyde. Oxidative stress in these cases can be induced by a variety of substances: tert-butyl hydroperoxide; cumene hydroperoxide; hydrogen peroxide; xanthine/xanthine oxidase; a mixture of ferrous sulfate and potassium ascorbate, and etc.

To initiate oxidative stress in the experiments, a mixture of ferrous sulfate and potassium ascorbate was used. In mitochondrial metabolism, a certain amount of $H_2O_2$ is formed, which under physiological conditions, is not dangerous as it is quickly utilized by various antioxidant systems. Addition of ferrous sulfate in combination with potassium ascorbate to a medium containing mitochondria causes a reaction of ferrous iron with $H_2O_2$ (the Fenton reaction) to form the highly reactive hydroxyl radical

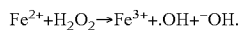

$$Fe^{2+}+H_2O_2 \rightarrow Fe^{3+}+\cdot OH+{}^-OH.$$

In turn, the hydroxyl radical reacts with unsaturated fatty acids in membranes and stimulates their free radical oxidation, ultimately leading to accumulation of malondialdehyde. Such a model is well suited for studying effectiveness of various antioxidants including compounds of general formula (I).

Figure 6:
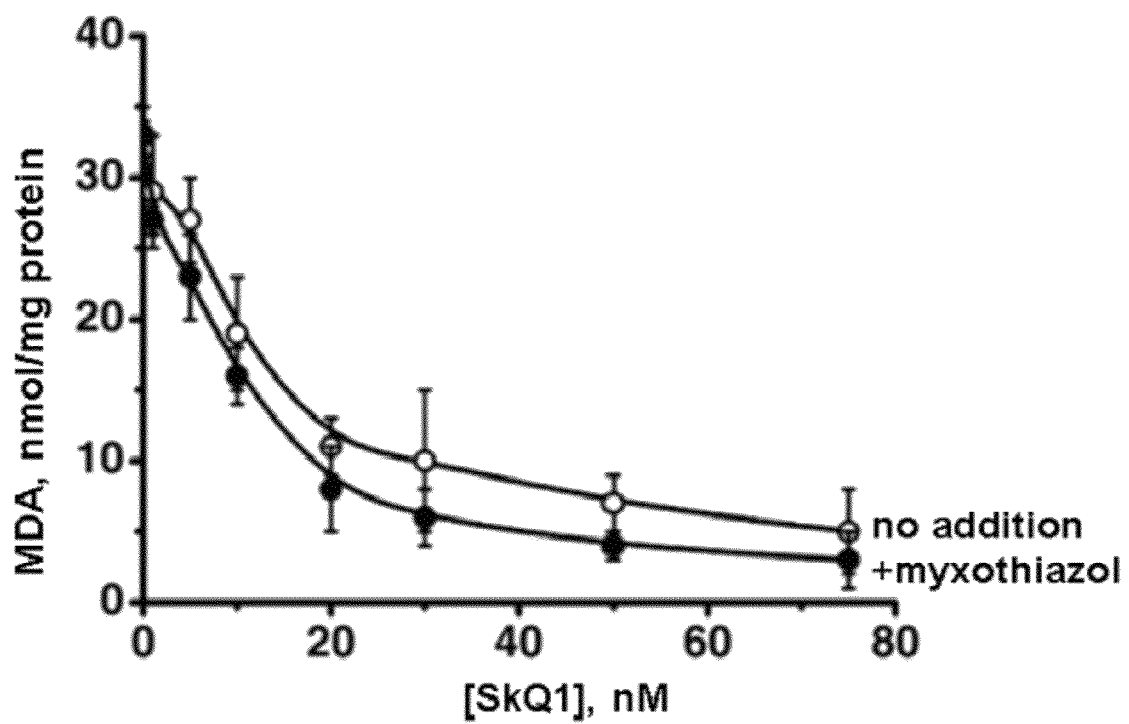
FIG. 6 is a graphic representation showing that SkQ1 protects mitochondria under conditions of oxidative stress caused by a mixture of ferrous sulfate with potassium ascorbate as measured by MDA.

FIG. 6 shows the results of testing the antioxidant activity of SkQ1. The highest antioxidant activity of SkQ1 is manifested at concentrations of 20 nM to 50 nM. Addition of myxothiazol (complex III inhibitor) to the mitochondrial suspension prevents the oxidation of SkQ1 with complex III that greatly improves the antioxidant capacity of SkQ1. The results confirm the antioxidant capacity of SkQ1, and moreover, show the importance of the ability of antioxidants to be reduced with the mitochondrial respiratory chain.

Thus, the method for quantitative measurement of malondialdehyde with a high degree of accuracy allows the prediction of pro-oxidant or antioxidant properties of test compounds as well as the testing of their effective concentrations.

Example 5

Antioxidant or Pro-Oxidant Activity of Mitochondria-Addressed Compounds in Animal, Plant, Bacterial, or Yeast Cell Cultures 1. Activity of Mitochondria-Addressed Compounds in Animal Cell Cultures.

Human uterine carcinoma cell line HeLa and normal human diploid fibroblasts derived from lung and skin were selected for testing the antioxidant capacity of compounds of general formula (I). Testing of the antioxidant capacity of the compounds was performed using the methods of cytofluometry and fluorescence microscopy.

In preliminary experiments for each cell culture, the optimal concentration of $H_2O_2$ which causes significant (60% to 80%) cell apoptosis with no visible signs of necrosis was selected. To determine the chromatin condensation and fragmentation which occurs in apoptotic cells, the fluorescent dye Hoechst was used. The dye at a concentration of 1 μg/ml was added to live or fixed cells at the end of a 30 min incubation. To determine necrosis, the fluorescent dye propidium iodide (PI) at a concentration of 2 μg/ml was added to non-fixed cells. The percentage of apoptotic and necrotic cells was determined by counting the number of cells with fragmented nuclei and cells permeable to propidium iodide, respectively.

In experiments with penetrating, mitochondria-addressed antioxidants, depending on penetrating ability of the compounds, the time necessary for their accumulation in mitochondria from cell culture may be different.

Figure 7:
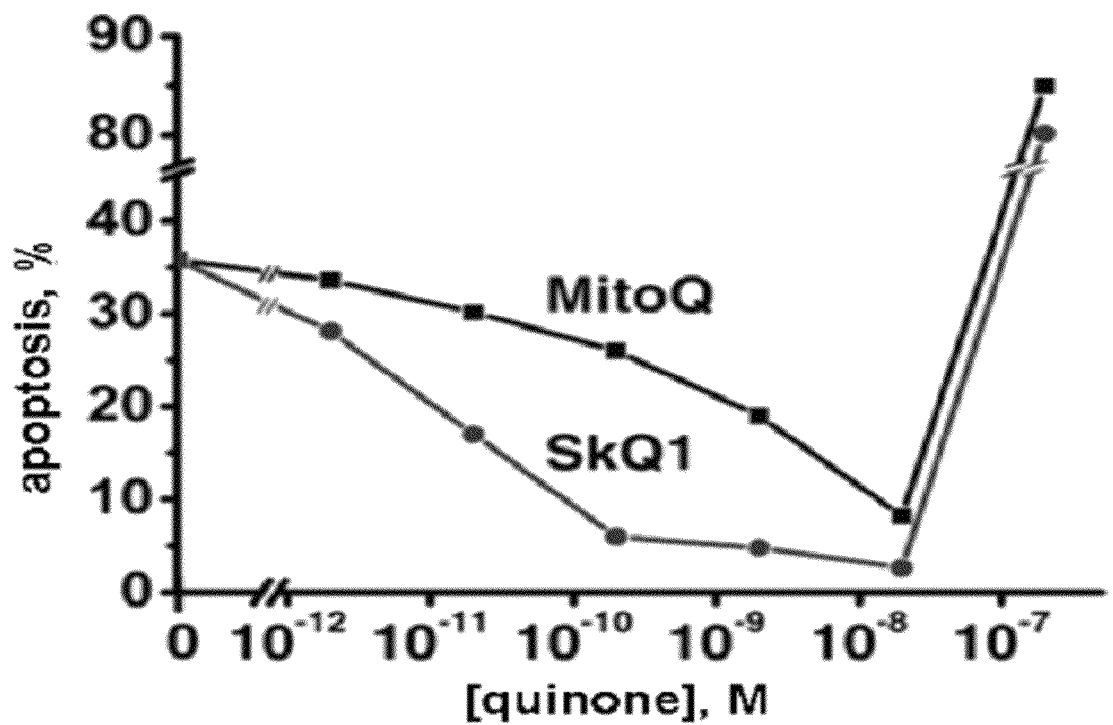
FIG. 7 is a graphic representation showing how incubation for 7 days with SkQ1 and MitoQ protect cells against death (% apoptosis) induced by H₂O₂ (300 μM)

SkQ1 and MitoQ increase resistance of cells to $H_2O_2$ after an incubation with the cells for 5 to 7 days. The oxidative phosphorylation uncoupler FCCP causing a decrease in mitochondrial membrane potential, prevented the protective effects of SkQ1 and MitoQ. This Control indicates that the tested compounds are indeed mitochondria-addressed. SkQ1 and MitoQ, being mitochondria-addressed antioxidants, exert their effects at very low concentrations. In particular, SkQ1 exerts its protective effect even at a concentration of 0.2 nM (FIG. 7). FIG. 7 also shows that SkQ1 protects cells against death much more effectively than MitoQ, i.e., SkQ1 is a more effective antioxidant. Like any antioxidants, SkQ1 and MitoQ have limiting concentrations above which they show pro-oxidant activity. In particular, at a concentration above 0.5 μM, SkQ1 and MitoQ manifest pro-oxidant activity leading to the stimulation of cell death induced by $H_2O_2$.

To measure the level of oxidative stress stimulated by $H_2O_2$, cells were stained with fluorescent dye DCF-DA (2′,7′-dichloro-dihydrofluorescein diacetate), and the level of fluorescence of the dye was measured with a cytofluorimeter.

Estimates were made on the basis of seven experiments. Data were estimated with respect to a group of the control cells lying on the diagram in the area of low DCF-DA fluorescence (50% of the population), this group of cells was taken as 100% and indicators for every action were estimated relative to this group.

Figure 8A:
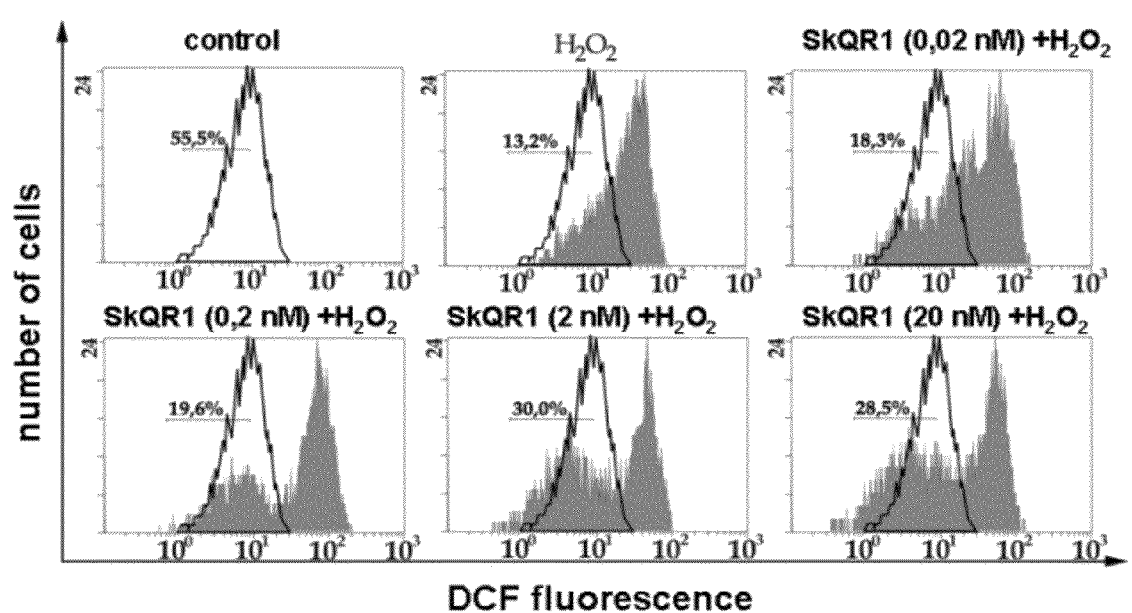
FIG. 8A is a series of graphic representations of fluorescent cytometric studies of HeLa cells incubated with different concentrations of SkQR1 for 2 hours to reduce the levels of oxidative stress in cells induced by H₂O₂ (300 μM), where cytofluometry data measuring the number of cells with low levels of oxidative stress was estimated.
Figure 8B:
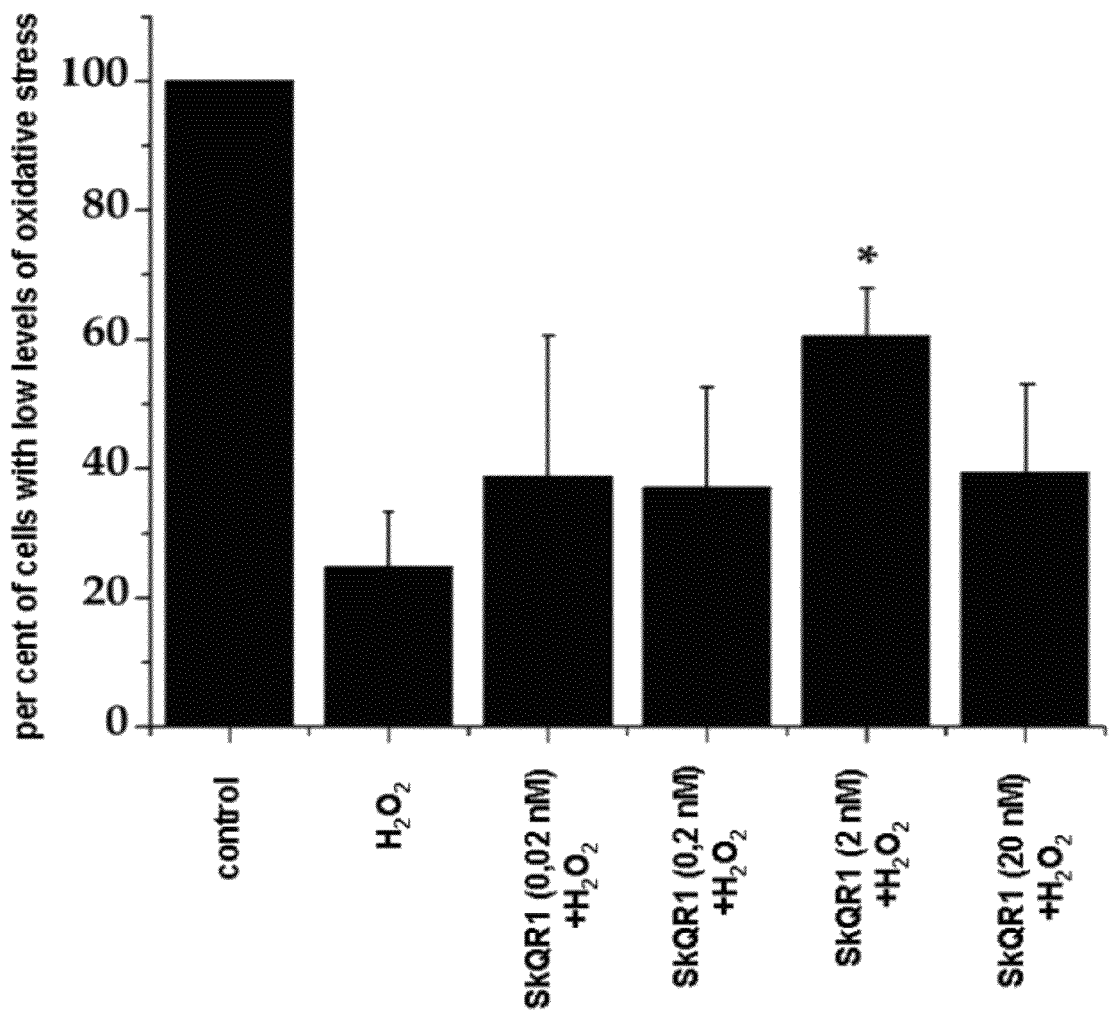
FIG. 8B is a graphic representation of the % cells with low levels of oxidative stress after the treatments indicated.
Figure 9:
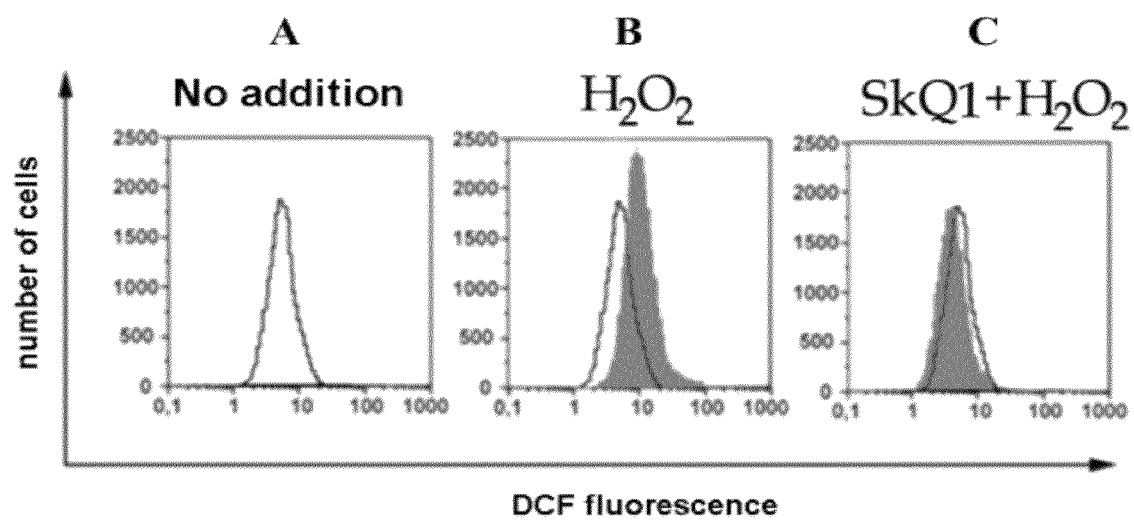
FIGS. 9A through 9C are graphic representations showing fluorescent cytometry of HeLa cells incubated with SkQ1 (20 nM) for 7 days (FIG. 9C), and measuring protection against oxidative stress induced by nothing (control) (FIG. 9A), and H₂O₂ (300 μM) (FIG. 9B).

With this method, it was shown that incubation of cells with SkQ1 or MitoQ for 1 to 5 hours did not prevent $H_2O_2$-induced oxidative stress in cells. At the same time, SkQR1 having higher penetrating ability (hydrophobic cation, the rhodamine G moiety, was used as the target group in place of tetraphenylphosphonium) has antioxidant activity within a given time window, and at lower concentrations than SkQ1 (FIG. 8A and FIG. 8B). SkQ1 (FIG. 9C) as well as MitoQ exhibited their antioxidant properties only after 5 to 7 days of incubation with the cells. The resulting time dependencies are well correlated with penetrating ability of SkQR1, SkQ1, and MitoQ; their penetrating abilities can be described by the following sequence: SkQR1>SkQ1>MitoQ.

Thus, the present methods allow the determination of the ability of compounds of general formula (I) to protect cells against death caused by oxidative stress. In addition, these methods help in predicting therapeutic doses and timing of administration of preparations based on compounds of general formula (I).

2. Activity of Mitochondria-Addressed Compounds in *E. coli*.

To test pro-oxidant and antioxidant properties of mitochondria-addressed compounds of general formula (I), a method for determining oxidative stress in *E. coli* cells was developed. For this purpose, a biosensor system was created based on luxAB genes encoding bacterial luciferases to study effect of penetrating ions on oxidative stress in a bacterial cell. High sensitivity, the ease of detection of a light signal with the use of a luminometer or scintillation counter, direct proportionality between the amount of the enzyme luciferase and bioluminescence intensity within a few orders of magnitude, a possibility of measuring both in vitro and in vivo (without damaging cells), and other benefits support application of luciferase genes in various genetic and biochemical tests.

In a method developed, genes encoding luciferase from terrestrial bacteria *Photorhabdus luminescens* were used [1]. Gram-negative bacteria *P. luminescens* are symbionts of entomopathogenic nematodes. Luciferase from *P. luminescens* is characterized by high thermal stability (it remains active at temperatures up to 45° C.) that facilitates the use of the lux genes as reporters.

To test chemical contaminants (toxicants) in water, soil, food, air etc., the lux-biosensors were used in two ways: bioluminescence quenching by the toxicant; and the induction (increase) of bioluminescent intensity by a toxicant.

Methods related to the first alternative include the use of a mechanism of inhibitory effect of toxic substances on cell metabolism, mainly on the respiratory chain, that indirectly affect the luciferase reaction, resulting in a decrease in the bioluminescent intensity of the cell suspension.

Methods related to the second alternative are based on the induction (increase) of intensity of cells bioluminescence induced by a toxicant. These methods include various options for the use of specific regulatory elements developed by bacteria in the process of evolution, and which are specifically responsive to the presence of a particular chemical substance in the environment. The above-mentioned group of biosensors provides both specificity and high sensitivity because they are based on the interaction of a receptor protein (repressor or activator) with a chemical compound. In bacteria, regulatory systems can be distinguished that specifically react to toxicants which act on: cell membranes; proteins; chromosome (DNA); and the induction of oxidative stress in a cell.

In addition, bacteria have regulatory systems which specifically react to heavy metals and arsenic ions. The grpE: $P_{grpE}$ promoter can be used as a biosensor for toxicants which act on cellular proteins (for example, various phenol derivatives, alcohols). This promoter is located in the bacterial genome upstream of heat shock genes and is activated only when modified, denatured proteins appear in a cell. The $P_{recA}$ SOS promoter is used as a biosensor for DNA-tropic agents (mitomycin C, methyl methanesulfonate, dioxins, as well as ultraviolet and ionizing radiation). The LexA protein is a repressor. The $P_{recA}$ recA promoter is activated only upon the induction of damage to the genome, i.e., to DNA molecules. The $P_{katG}$ and $P_{soxS}$ promoters are used to detect substances inducing oxidative stress in a cell (forming the hydroxyl radical, OH, the superoxide ion-radical, $O_2^-$, and hydrogen peroxide, $H_2O_2$). The $P_{katG}$ promoter (activator OxyR) specifically reacts to hydrogen peroxide, organic peroxides etc. The $P_{soxS}$ promoter is activated when superoxide ion-radical appears in the environment. The lux-biosensors were developed on the basis of these inducible promoters.

All the promoters used in the method, with corresponding regulatory regions, were obtained from the genome of the *E. coli* K12 MG1655 bacteria by the PCR method with the use of specific synthesized primers. A non-promoter vector with the pBR322 replicon and bla gene responsible for resistance to ampicillin (selective marker) was used as a vector. The promoter region was embedded into the plasmid at the EcoRI-BamHI sites. The lux operon of *Ph. luminescens* consisting of five genes, luxCDABE, was selected as the lux cassette.

All the biosensors were tested for suitability to work with MAAs of general formula (I). MAAs of general formula (I), in particular, SkQ1 and MitoQ, are most likely to have high specificity to biosensors related to oxidative stress, as their structures comprise quinone derivatives and they accumulate in charged membranes with high efficiency. Therefore, the use of the pLUX::PkatG and pLUX::PsoxS biosensors are optimal. DNA damage fixation in oxidative stress and the effect of penetrating ions on this process are possible when the pLUX::PrecA biosensor is used. The pLUX::PgrpE and pLUX::Plac biosensors are used as positive and negative controls, respectively.

Figure 10A:
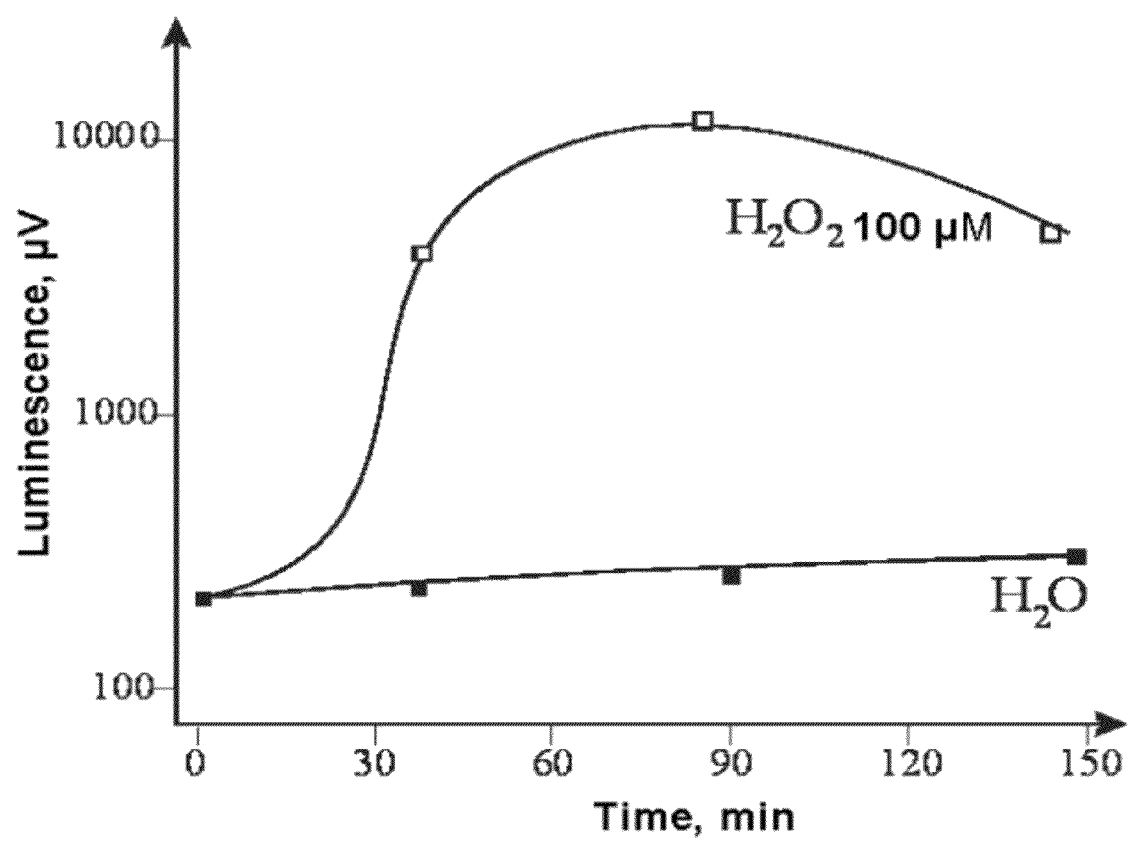
FIGS. 10A and 10B are graphic representations showing luminescence induction in *E. coli* MG1655 pLUX::PsoxS in the presence of H₂O₂ (100 μM) (FIG. 10A) and paraquat (PA) (100 μM) (FIG. 10B), or water.
Figure 10B:
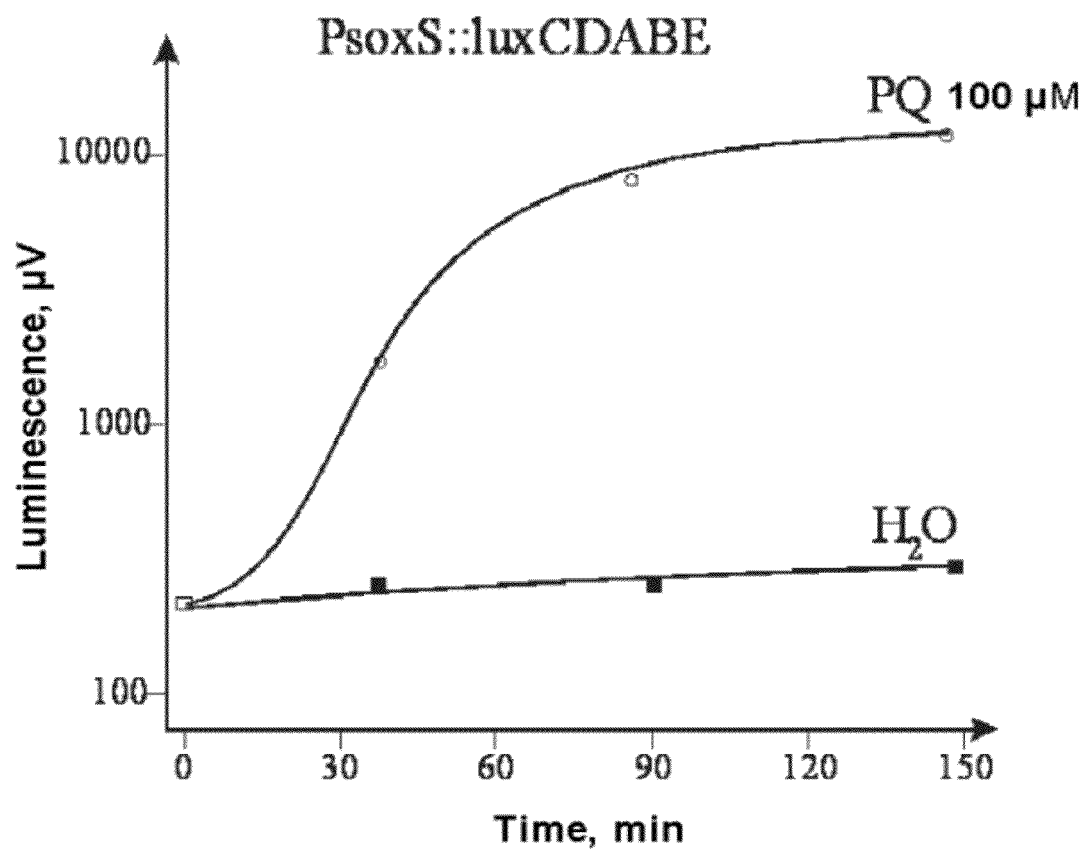

In the first phase of testing, conditions for oxidative stress induction at which the maximum induction of luminescence occurs, were selected. FIGS. 10A and 10B show the ability of $H_2O_2$ (FIG. 10A) and paraquat (FIG. 10B) to induce bioluminescence of biosensor. Induction of luminescence in *E. coli* MG1655 pLUX::PkatG in the presence of $H_2O_2$ becomes evident within 15 minutes and reaches a maximum value for one hour (FIG. 10A). The ratio of the intensity of luminescence between control cells and induced cells is 1/80 at optimal concentrations of $H_2O_2$. Induction of luminescence in *E. coli* MG1655 pLUX::PsoxS in the presence of paraquat becomes evident within 15-20 minutes and reaches a maximum value for two hours (FIG. 10B). The ratio of the intensity of luminescence between control cells and induced cells is 1/100 at optimal concentrations of paraquat.

Figure 11:
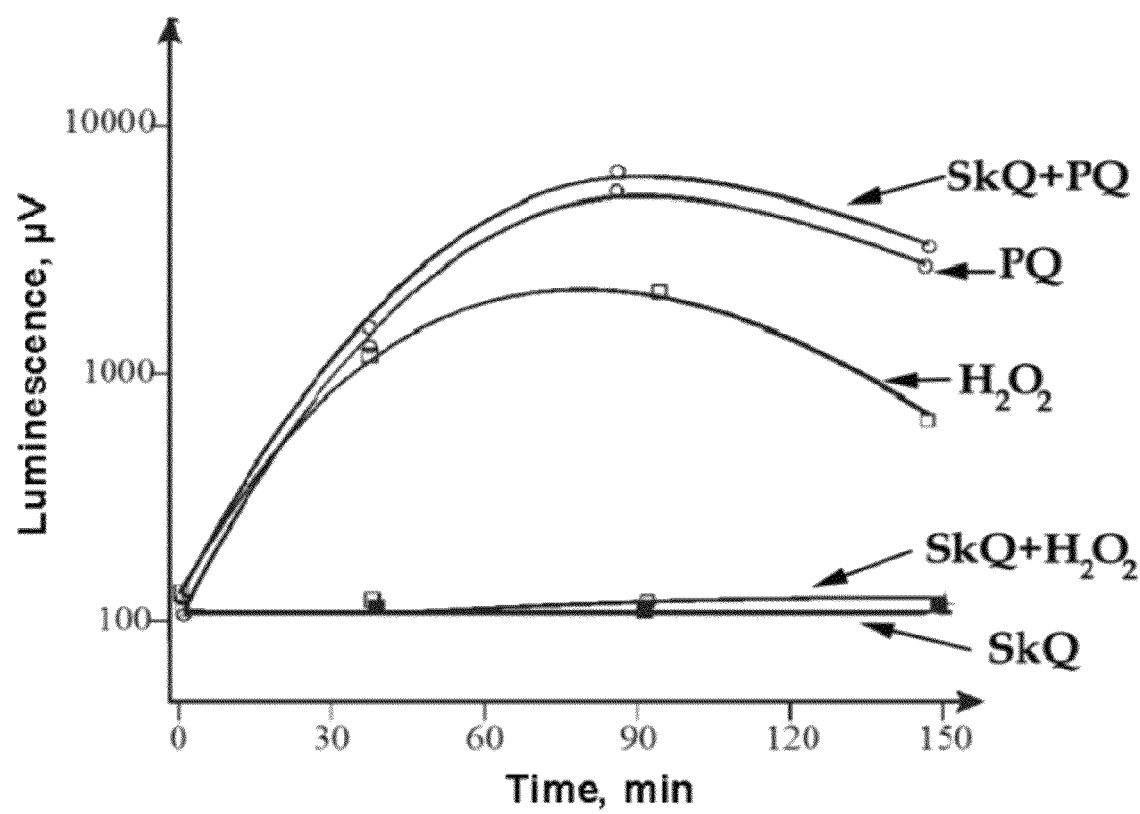
FIG. 11 is a graphic representation showing the induction of the soxS promoter by H₂O₂ (500 μM) and paraquat (PA) (100 μM) in the absence or presence of SkQ (10 μM).

At the next stage, pro-oxidant or antioxidant capacities of compounds of general formula (I) was tested. With the help of the pLUX::PkatG and pLUX::PsoxS biosensors, antioxidant properties of SkQ under conditions of oxidative stress in *E. coli* were tested. 10 μM SkQ efficiently protects a cell against superoxide anion radicals resulting from oxidative stress induced by hydrogen peroxide, while the concentration of SkQ had no appreciable effect on oxidative stress induced by paraquat (FIG. 11). This discrepancy may be due to different ways of generation of reactive oxygen species by hydrogen peroxide and paraquat. With hydrogen peroxide, oxidative stress is induced for a short time ($H_2O_2$ is actively decomposed by antioxidant defense enzymes in a cell), whereas with paraquat, oxidative stress lasts much longer. In addition, in the E. coli cells, the multidrug resistance (MDR) system which exports positive cations out of a cell actively functions. The activity of these enzymes dramatically reduces the efficacy of SkQ and its analogs (i.e., SkQ1). Thus, with $H_2O_2$, SkQ1 has time to protect cells against oxidative stress, prior to be exported out of a cell by MDR proteins, whereas with paraquat, SkQ1 is no longer effective.

These results showed that the developed test method is a useful tool for testing pro-oxidant or antioxidant capacity of compounds of general formula (I).

Example 6

In Vivo Testing of Biological Activity of Compounds of General Formula (I) in Animals and Plants In vivo testing of compounds of general formula (I) in animals or plants is done using only those compounds which have passed all previous testing (supra) and have demonstrated potential biological activity. For in vivo experiments at the pre-selection stage, the simplest methods that allow the evaluation of drugs for biological activity are used. For this purpose, small invertebrates such as the crustaceans *Ceriodaphnia affinis* can be used as a model. Such organisms, in particular, zooplankton, serve as a popular test for the estimation of environmental pollution, study on biological effects of extracts of materials, food products, medical preparations. Such tests take into consideration survival, behavior of test objects, and violations of certain physiological functions. For identification of effects of weak influences in chronic mode, apart from said parameters, such integral individual parameters as growth and reproduction are also under control.

In quantifying the effect of chemical agents on test organisms in a chronic mode, the phase character of toxic effect, i.e. alternation of depression and stimulation of activity of a biological function or development of a structural element caused by potentially toxic substances, is manifested. As a result, many potential toxicants at certain concentrations may have a temporary stimulating effect on certain functions and on a test object in its entirety. Thus, a criterion for a favorable effect of the compounds is a measure of the life span of the test organism because in this case, the risk of being in a favorable phase of the preparation, which is really toxic, can be excluded.

The effect of preparations of SkQ1 at different concentrations on basic life functions of the crustaceans *Ceriodaphnia affinis* for the duration of their natural life was studied with particular attention to stimulating effect of the preparation.

In the first series of experiments, survival of the crustaceans (20 in each series) in the presence of ethanol (0.79 mg/l) did not differ from control. As shown in Tables I and II below, concentrations of 5.5 nM and 0.55 nM SkQ1, survival of the crustaceans was higher than control, whereas at a concentration of 55 nM, survival was lower than control. Time of death in a fixed population of the crustaceans at concentrations of 0.55 nM and 5.5 nM SkQ1 increased during the entire observation period, whereas time of death in 50% exceeded the parameter in control 2 and 1.4 times, respectively (Table 1).

TABLE 1

Fixed time (days) of death of *Ceriodaphnia affinis* caused by SkQ1

| Substance/Concentration | $LT_{25\%}$ | $LT_{50\%}$ | $LT_{75\%}$ |
|---|---|---|---|
| Control | 16 | 18 | 29 |
| Ethanol, 0.79 mg/l | 14 | 18 | 25 |
| SkQ1, 0.55 nM | 22 | 36 | 45 |
| SkQ1, 5.5 nM | 18 | 26 | 46 |
| SkQ1, 55 nM | 9 | 12 | 17 |

The average life span of the crustaceans treated with SkQ1 concentrations of 0.55 nM and 5.5 nM was longer than control, and at a concentration of 55 nM SkQ1 and lower, these differences were statistically significant (Table 2).

TABLE 2

Average Life Span of *Ceriodaphnia affinis* Treated With SkQ1

| Substance/Concentration | M ± m | $t_d$ | % of control |
|---|---|---|---|
| Control | 20.2 ± 4.99 | | |
| Ethanol, 0.79 mg/l | 19.55 ± 5.26 | 0.18 | 96.78 |
| SkQ1, 0.55 nM | 33.55 ± 6.21 | 3.28* | 166.09 |
| SkQ1, 5.5 nM | 31.25 ± 8.11 | 2.27* | 154.7 |
| SkQ1, 55 nM | 12.85 ± 2.79 | 2.52* | 63.61 |

*difference is statistically significant

These the results indicate the ability of SkQ1 to have beneficial effects on the activity of small invertebrates resulting in increasing their life span. In addition, the concentrations of SkQ1 that had a beneficial effect on an organism can be used in experiments to test biological activity of test preparations of general formula (I) in higher animals.

Example 7

Method for Purification of Mitochondria-Addressed Antioxidant Using 'Molecular Trap'

Initial technical product PDTP (5 g) after silica gel pretreatment in ethanol-chloroform (1:9) system has a purity of about 85%. The content of the reduced form of the product is 8%.

To remove basic impurities, an HPLC method with a $C_{18}$ column, 500×45 mm was used. The mobile phase was salt-free, unbuffered, water-ethanol solution in gradient mode (System A: 15% ethanol, system B: 40% ethanol). After collection of central fractions, the purity of the preparation is about 92%. The content of the reduced form is 6%.

Comparative qualitative reaction of the initial and purified products to bromides shows retention of bromide ion after chromatographic purification. Analytical HPLC on a $C_{18}$ column, 250×4.6 mm in a system of 0.05% trifluoroacetic acid in 65% acetonitrile in water also shows approximately the same peak intensity of bromide ion (at the beginning of the chromatogram) for initial and purified product.

After purification by HPLC (3.8 g), solvent evaporation, and drying under a high vacuum, the product has a form of thick, clear oil, dark brown in color. To minimize the content of the reduced form in the preparation, a variant of the molecular trap method was used.

A flask of oil is mixed with 200 ml hexane. 5 ml acetone is then added, and the mixture is stirred vigorously with a magnetic stirrer for 30 min. The solvent layer is carefully decanted off. A chromatographic control of the decanted portion of the solvent and the remaining oil is made. The HPLC chromatogram of solvent contains a small peak of acetone and only an intense peak of the reduced form; the main oxidized form is not present. The chromatogram of the desired product shows clearly decrease in the content of the reduced form.

To further minimize the content of the reduced form, the procedure may be repeated several times. The procedure may be carried out in automatic mode with continuous feed of fresh solvent and disposal of used solution. Using this method, there is no loss of basic substance. Bromide ion is preserved.

The purity of the product is about 97%. The content of the reduced form is not more than 1.0%.

Purification using gel chromatography in an ethanol solution may be used as a final stage prior to dosage bottling of concentrated solution of the preparation, drying it and storing it. Approximately 3.7 g of the preparation is dissolved in 5 ml to 6 ml of ethanol and subjected to chromatography on a 600 mm×10 mm column of Sephadex LH-20 pre-equilibrated with absolute ethanol (Spectrophotometric Grade). Head and tail fractions are discarded.

The purity of the main faction is at least 98%. The content of the reduced form is 0.8% to 0.9%. The concentration of the preparation can reach 150 mg/ml to 200 mg/ml. This solution is convenient for preparation of aliquots and drying of the substance in the final form.

Example 8

Synthesis of Plastoquinonyl-Decyl-Triphenylphosphonium (PDTP) Bromide

The synthesis of PDTP involves the following steps: (1) oxidation of 2,3-dimethylphenol (1) to 2,3-dimethyl-1,4-benzoquinone (2) with the Jones reagent; (2) Attachment of 11-bromo-undecanoic acid (3) to triphenylphosphine with the formation of (10-carboxy-decyl)triphenylphosphine bromide (4); and formation of the desired compound (5) by the reaction of the produced compound (4) with 2,3-dimethyl-1,4-benzoquinone (2) in the presence of silver nitrate and ammonium persulfate. The scheme of the synthesis is shown in FIG. 13.

(1) Synthesis of 2,3-Dimethyl-1,4-Benzoquinone (2)

The Jones reagent (solution of 110 g (0.37 mol) of $Na_2Cr_2O_7 \times 2H_2O$ in a mixture of 157 ml of water and 70 ml of concentrated sulfuric acid) was added with stirring to a solution of 20 g (0.16 mol) of 2,3 dimethylphenol in 230 ml of ether and the mixture was stirred for 24 hours. The mixture was extracted with ether, the combined ether extracts were washed and then dried with calcined magnesium sulfate and after removal of the solvent on a rotary evaporator the residue was subjected to flash chromatography on silica gel in chloroform.

The yield of compound 2 in a form of yellow crystalline substance was 8.7 g (40%).

TCX: $R_f(CHCl_3)$=0.46; HPLC: τ=17.4 min (0% to 90% B for 26.4 min; A: 10 mM $H_3PO_4$, B: AcCN), m.p. 58° C. (56.5-57.5° C.)[1]; UV ($CH_3OH$): λmax 209 nm, 256 nm, 344 nm; ESI MS: m/z calculated for $C_8H_8O_2$ 136.15. found 136.2.

(2) Synthesis of (10-Carboxy-Decyl)Triphenylphosphine Bromide (4)

588 mg (2.24 mmol) of triphenylphosphine was added to 530 mg (2 mmol) of 11-bromo-undecanoic acid and the mixture was kept in a sealed tube at 85° C. for 12 hours. Then the mixture was subjected to separation on a silica gel column in a system of chloroform-methanol (9:1). The yield of compound 4 in a form of clear oil was 895 mg (85%).

TCX: $R_f$ 0.52 (chloroform-methanol, 4:1); HPLC: τ=7.28 min (5% to 95% B for 11.5 min; A: 0.1% TFA; B: 0.1% TFA in acetonitrile); UV spectrum (0.1% TFA-acetonitrile, 38:62): $\lambda_{max}$ 200 nm, 224 nm, 268 nm; ESI MS: calculated for $C_{29}H_{36}OP$: 447.6. found m/z 448.2 ($MH^+$; 100%).

(3) Synthesis of [10-(4,5-Dimethyl-3,6-Dioxo-Cyclohexa-1,4-Dien-1-yl)Decyl]-Triphenylphosphonium Bromide (PDTP) Bromide (5)

A solution of 228 mg (1 mmol) ammonium persulfate in 5 ml of water was added to a solution of 135 mg (1 mmol) (compound 2), 526 mg (1 mmol) (compound 4) and 85 mg (0.5 mmol) silver nitrate in 40 ml of a mixture of acetonitrile and water (1:1) at 80° C. to 90° C. The mixture was heated with stirring at the same temperature for 12 hours. The mixture was diluted with water and extracted with dichloromethane. After evaporation of dichloromethane to a small (concentrated) volume, the product was precipitated with diethyl ether. The solution was decanted from the precipitate, and the precipitate was reprecipitated several times. The precipitate was then purified on a silica gel column in a mixture of dichloromethane-ethanol (in a ratio of 9:1).

The yield of [10-(4,5-dimethyl-3,6-dioxo-cyclohexa-1,4-dien-1-yl)decyl]-triphenylphosphonium bromide (PDTP bromide) was 35%.

TCX: $R_f$(CHCl3-CH3OH, 4:1)=0.66; HPLC: τ=10.1 min (5% to 95% B for 12 min; A: 0.05% TFA, B: 0.05% TFA in AcCN); UV ($CH_3OH$): λmax 198 nm, 226 nm, 260 nm ($\epsilon_{260}$=18652 cm-1*M-1), 352 nm; ESI MS: m/z calculated for $C_{36}H_{42}O_2P$ 537.69. found 537.3.

Example 9

Synthesis of Mitochondria-Addressed Compounds which are Useful Antioxidants

The structures of berberine and palmatine SkQ derivatives 1-4 are shown below:

SkQB

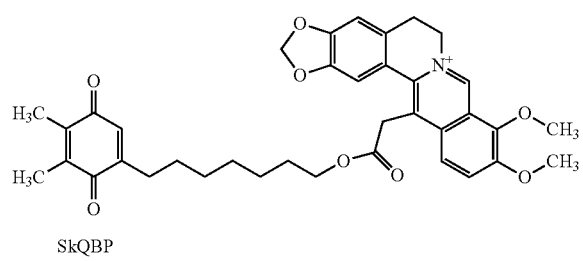

1

SkQBP

-continued
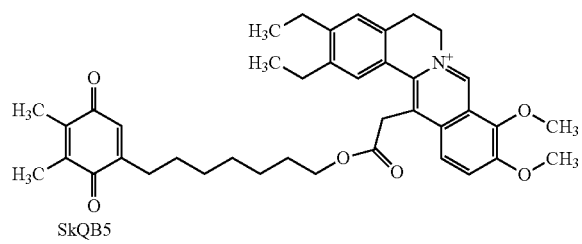
SkQB5
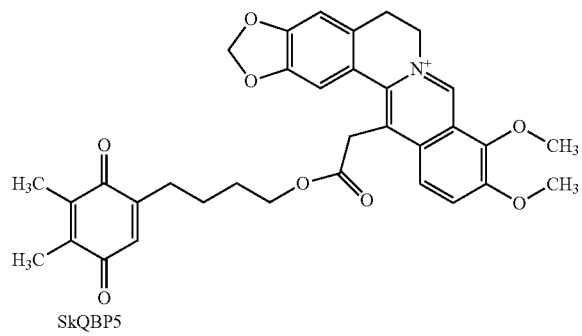
SkQBP5
-continued
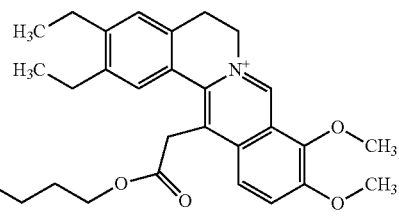
The scheme for the synthesis of 9,10-dimethoxy-13-[7-(4,5-dimethyl-3,6-dioxo-cyclohexa-1,4-dien-1-yl)heptyloxy-carbonyl-methyl]-5,6-dihydrobenzo[g]-1,3-benzodioxole[5,6-c]quinolizinium bromide, 1 (13-[7-(4,5-dimethyl-3,6-dioxo-cyclohexa-1,4-dien-1-yl)heptyloxycarbonyl-methyl] berberine bromide) is shown below:
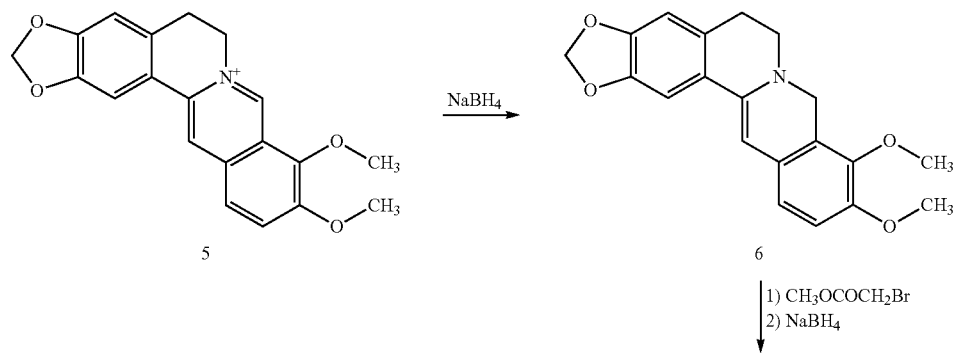
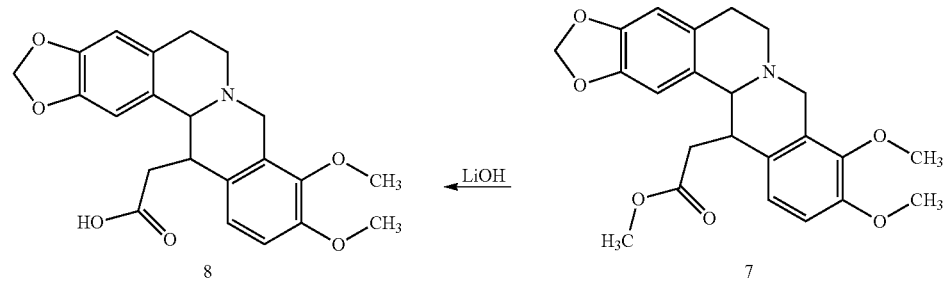

-continued

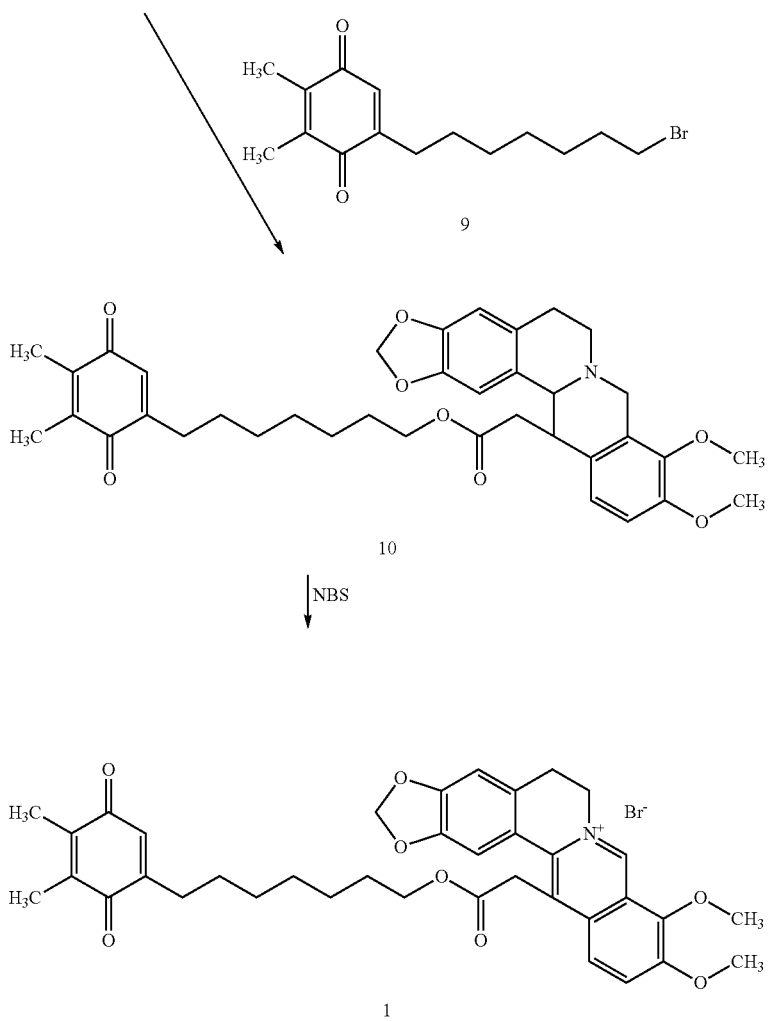

Compound 1 was produced from berberine bisulfate (5) which was reduced with sodium borohydride in pyridine for 30 min, RT and crystallization from water to yield compound 6 was produced with 91% yield. Compound 6 was alkylated with bromoacetic acid methyl ester (1 hour, 100° C.), followed by reduction of the intermediate compound with sodium borohydride (30 min, RT) to give compound 7 which was isolated by extraction with ether from an aqueous solution (80% yield) and saponified by 1% water-methanol solution of lithium hydroxide by boiling for 1.5 hours to give compound 8. After crystallization from water, the yield of compound 8 was 61%. Compound 8 was converted into cesium salt which was condensed with previously synthesized derivative of 2,3-dimethyl-1,4-benzoquinone 9 at 60° C. for 48 hours. Compound 10 was oxidized with N-bromosuccinimide (NBS) in methylene chloride solution for 1 hour, following removal of excess NBS by washing the organic phase with water and its drying. The mixture was evaporated and the final compound 1 was precipitated with ether. Purification of compound 1 was performed by HPLC (C18) in a gradient of acetonitrile containing 0.05% TFA, in 0.05% aqueous TFA from 30 to 80%. After the last two stages, the overall yield was 50%.

Compounds 2-4 were similarly produced starting with palmatine:

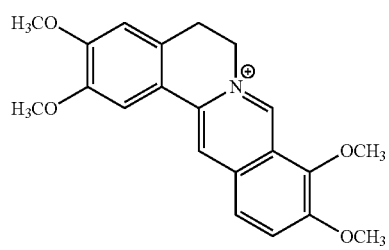 [SMILES: COc1cc2c(cc1OC)-c1cc3ccc(OC)c(OC)c3c[n+]1CC2]

Characteristics of the compounds 1-5 produced are as follows:

Compound 1: 13-[7-(4,5-dimethyl-3,6-dioxo-cyclohexa-1,4-dien-1-yl)heptyloxycarbonyl-methyl]berberine (SkQB): TCX: $R_f$ (chloroform-methanol, 65:10)=0.16; $R_f$ (chloroform-methanol, 4:1)=0.39. HPLC: τ=8.98 min (5% to 95% B for 11 min; A: 0.05% TFA, B: 0.05% TFA in MeCN; Luna C18(2)' 0.46×15 cm, 5 μm, 1 ml/min). UV (ethanol): λmax 262 nm, 350 nm ($\epsilon_{350}$=23850 $cm^{-1}*M^{-1}$), 430 nm ($\epsilon_{430}$=5278 cm$^{-1}$*M$^{-1}$). ESI MS: m/z calculated for C$_{37}$H$_{40}$NO$_8$ 626.72. found 626.69.

Compound 2: 13-[7-(4,5-dimethyl-3,6-dioxo-cyclohexa-1,4-dien-1-yl)heptyloxycarbonyl-methyl]palmatine: (SkQBP1) TCX: R$_f$(chloroform-methanol, 65:10)=0.16; R$_f$ (chloroform-methanol, 4:1)=0.39. UV (ethanol): λmax 262 nm, 350 nm, 430 nm. ESI MS: m/z calculated for C$_{38}$H$_{44}$NO$_8$ 642.76. found 642.29.

Compound 3: 13-[4-(4,5-dimethyl-3,6-dioxo-cyclohexa-1,4-dien-1-yl)butyloxycarbonyl-methyl]berberine (SkQB5): TCX: R$_f$ (chloroform-methanol, 65:10)=0.23; R$_f$ (chloroform-methanol, 4:1)=0.39. HPLC: τ=7.71 min (5% to 95% B for 11 min; A: 0.05% TFA, B: 0.05% TFA in MeCN; Luna C18(2)' 0.46×15 cm, 5 μm, 1 ml/min). UV (ethanol): λmax 262 nm, 350 nm, 430 nm. ESI MS: m/z calculated for C$_{34}$H$_{34}$NO$_8$ 584.64. found 584.22.

Compound 4: 13-[4-(4,5-dimethyl-3,6-dioxo-cyclohexa-1,4-dien-1-yl)butyloxycarbonyl-methyl]palmatine (SkQBP5): TCX: R$_f$(chloroform-methanol, 65:10)=0.23; R$_f$ (chloroform-methanol, 4:1)=0.39. HPLC: τ=7.73 min (5% to 95% B for 11 min; A: 0.05% TFA, B: 0.05% TFA in MeCN; Luna C18(2)' 0.46×15 cm, 5 μm, 1 ml/min). UV (ethanol): λmax 262 nm, 350 nm, 430 nm. ESI MS: m/z calculated for C$_{35}$H$_{38}$NO$_8$ 600.68. found 600.87.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A purified pharmaceutical preparation comprising oxidized SkQ1, said oxidized SkQ1 having the structure:

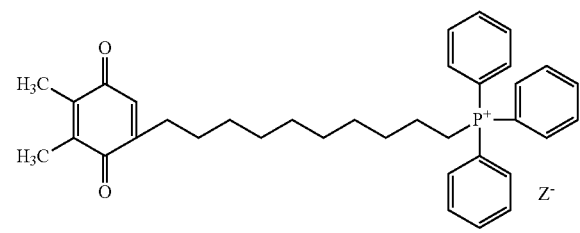 [SMILES: CC1=C(C)C(=O)C(CCCCCCCCCC[P+](c2ccccc2)(c2ccccc2)c2ccccc2)=CC1=O]

with the provisos that:
no individual impurity exceeds 1.5% of the preparation;
the total impurity content of the preparation does not exceed 4.0%; and
the content of reduced SkQ1 is not greater than 10%, said reduced SkQ1 having the structure:

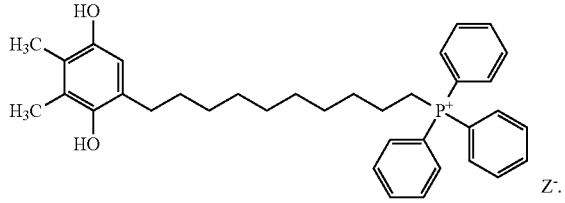 [SMILES: Cc1c(O)cc(CCCCCCCCCC[P+](c2ccccc2)(c2ccccc2)c2ccccc2)c(O)c1C]

2. The preparation of claim 1, which is stable at room temperature for at least 1 year.
3. The preparation of claim 1, which is stable at room temperature for at least 2 years.
4. The preparation of claim 1, which is stable at 2° C. to 8° C. for at least 2 years.
5. The preparation of claim 1, which is stable at or below 0° C. for at least 2 years.
6. A method of synthesizing a preparation comprising reduced and oxidized SkQ1, reduced SkQ1 being present at not greater than 10%, and oxidized SkQ1 being present at not less than 90%, comprising:
oxidizing 2,3-dimethylphenol to 2,3-dimethyl-1,4-benzoquinone;
linking 11-bromo-undecanoic acid to triphenylphosphine to form 10-carboxy-decyltriphenylphosphine; and
reacting 10-carboxy-decyltriphenylphosphine with 2,3-dimethyl-1,4-benzoquinone in the presence of silver nitrate and ammonium persulfate to form reduced and oxidized SkQ1; and
purifying the oxidized and reduced SkQ1,
the structure of reduced SkQ1 being:

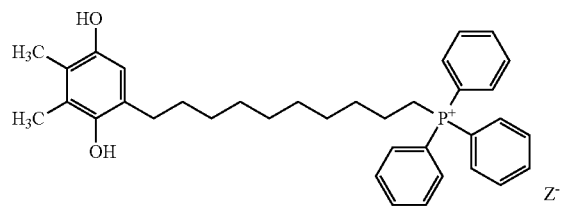 [SMILES: Cc1c(O)cc(CCCCCCCCCC[P+](c2ccccc2)(c2ccccc2)c2ccccc2)c(O)c1C]

and the oxidized form of SkQ1 being present at not less than 90%, the structure of oxidized SkQ1 being:

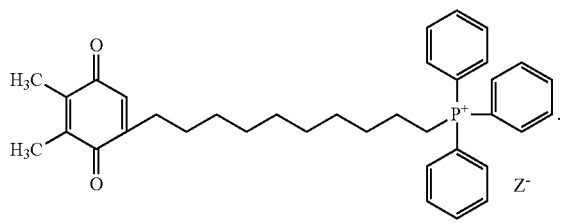 [SMILES: CC1=C(C)C(=O)C(CCCCCCCCCC[P+](c2ccccc2)(c2ccccc2)c2ccccc2)=CC1=O]

* * * * *